(12) United States Patent
Huang et al.

(10) Patent No.: US 12,727,876 B2
(45) Date of Patent: Sep. 8, 2026

(54) SURGICAL GUIDEWIRE DEVICE AND SUTURE FIXATION SYSTEM

(71) Applicant: Astron Medtech Corporation, Wilmington, DE (US)

(72) Inventors: Yi-Hsi Huang, Taipei City (TW); I-Lin Tsai, Taipei City (TW); Kuei-Hua Chen, Taipei City (TW)

(73) Assignee: Astron Medtech Corporation, Wilmington, DE (US)

( * ) Notice: Subject to any disclaimer, the term of this patent is extended or adjusted under 35 U.S.C. 154(b) by 0 days.

(21) Appl. No.: 19/431,626

(22) Filed: Dec. 23, 2025

(65) Prior Publication Data

US 2026/0114863 A1 Apr. 30, 2026

Related U.S. Application Data

(63) Continuation of application No. 19/268,611, filed on Jul. 14, 2025, now Pat. No. 12,508,017, which is a continuation of application No. 18/971,254, filed on Dec. 6, 2024.

(60) Provisional application No. 63/652,404, filed on May 28, 2024.

(51) Int. Cl.

| | |
|---|---|
| ***A61B 17/04*** | (2006.01) |
| ***A61B 90/00*** | (2016.01) |
| *A61B 17/00* | (2006.01) |
| *A61B 17/06* | (2006.01) |

(52) U.S. Cl.

CPC ...... *A61B 17/0469* (2013.01); *A61B 17/0482* (2013.01); *A61B 17/0485* (2013.01); *A61B 90/03* (2016.02); *A61B 2017/00367* (2013.01); *A61B 2017/00477* (2013.01);

(Continued)

(58) Field of Classification Search

CPC ........ D05B 87/00; D05B 87/02; D05B 87/04; A61B 17/0469; A61B 17/0482; A61B 17/0485; A61B 90/03; A61B 2017/00367; A61B 2017/00477; A61B 2017/00862; A61B 2017/06019; A61B 2090/034

See application file for complete search history.

(56) References Cited

U.S. PATENT DOCUMENTS 4,667,860 A * 5/1987 Feuerman .............. D05B 85/00 223/102
5,037,433 A 8/1991 Wilk (Continued)

OTHER PUBLICATIONS

Achilles PARS SutureTape WithAchilles Midsubstance SpeedBridge™ Implant System—Surgical Technique, Arthex, 2019 16 pages.

(Continued)

*Primary Examiner* — Phong Son H Dang
(74) *Attorney, Agent, or Firm* — Knobbe, Martens, Olson & Bear, LLP

(57) ABSTRACT

A surgical guidewire device includes an outer tube and a guide needle. The outer tube has a needle tip formed at a tube distal end of the outer tube. The guide needle is movably disposed in the outer tube and has a needle eye structure. When the surgical guidewire device is in use, a suture extends through the needle eye structure, and is carried through the outer tube along with the needle eye structure as the guide needle is moved relatively toward the tube distal end and then away from the outer tube.

8 Claims, 28 Drawing Sheets

(52) U.S. Cl.
CPC ............... *A61B 2017/00862* (2013.01); *A61B 2017/06019* (2013.01); *A61B 2090/034* (2016.02)

(56) References Cited

U.S. PATENT DOCUMENTS

| | | | | |
|---|---|---|---|---|
| 5,336,231 A * | 8/1994 | Adair | A61B 18/00 | 606/1 |
| 5,501,691 A * | 3/1996 | Goldrath | A61B 17/0483 | 604/158 |
| 5,782,845 A * | 7/1998 | Shewchuk | A61B 17/04 | 606/139 |
| 8,876,842 B2 * | 11/2014 | Marshall | A61B 17/0469 | 606/144 |
| 9,055,940 B2 * | 6/2015 | Chin | A61B 17/3474 | |
| 9,706,983 B1 * | 7/2017 | Alghamdi | A61B 17/06004 | |
| 11,213,284 B2 * | 1/2022 | Chin | A61B 17/0467 | |
| 11,344,295 B2 * | 5/2022 | Gustafson | A61B 17/0469 | |
| 11,950,775 B2 * | 4/2024 | Sartawi | A61B 17/06066 | |
| 12,508,017 B2 | 12/2025 | Huang | | |
| 2005/0021055 A1 * | 1/2005 | Toubia | A61B 17/0057 | 606/144 |
| 2007/0060931 A1 * | 3/2007 | Hamilton | A61B 17/0469 | 606/144 |
| 2007/0149987 A1 * | 6/2007 | Wellman | A61B 17/0057 | 606/148 |
| 2007/0179509 A1 * | 8/2007 | Nagata | A61B 17/0482 | 606/144 |
| 2008/0169320 A1 | 7/2008 | Fujiwara | | |
| 2008/0255591 A1 * | 10/2008 | Harada | A61B 17/0485 | 606/139 |
| 2009/0277934 A1 * | 11/2009 | Youngman | D05B 87/02 | 223/99 |
| 2009/0281569 A1 * | 11/2009 | AlGhamdi | A61B 17/06166 | 606/228 |
| 2012/0071896 A1 | 3/2012 | Ferree | | |
| 2013/0008076 A1 * | 1/2013 | Stenklyft | A01K 97/06 | 43/44.83 |
| 2020/0360012 A1 | 11/2020 | Heneveld | | |
| 2021/0025093 A1 * | 1/2021 | Gupta | D05B 91/00 | |
| 2022/0145505 A1 | 5/2022 | Gupta | | |
| 2025/0137180 A1 * | 5/2025 | Monjo | D05B 87/00 | |
| 2025/0366846 A1 | 12/2025 | Huang | | |
| 2025/0366847 A1 | 12/2025 | Huang | | |

OTHER PUBLICATIONS

Arthrex—The PARS Achilles Jig, The Less Invasive Achilles Repair, 2012, 4 pages.

* cited by examiner

SURGICAL GUIDEWIRE DEVICE AND SUTURE FIXATION SYSTEM

PRIORITY

This application is a continuation of U.S. non-provisional application Ser. No. 19/268,611, filed Jul. 14, 2025, which is a continuation of U.S. non-provisional application Ser. No. 18/971,254, filed Dec. 6, 2024, all of the contents of which are incorporated by reference herein in its entirety.

FIELD OF INVENTION

The disclosure is related to a surgical device, especially to a surgical guidewire device.

BACKGROUND OF THE INVENTION

During a traditional surgical operation, healthcare personnel generally require to create an incision on the surface of a patient's skin in order to insert surgical instruments into a wound site of the patient's body through the incision, and perform surgery and suturing.

In order to shorten the recovery time of the patient and reduce the size of the incision, a minimally invasive surgery has been developed. However, due to the small size of the incision in minimally invasive surgery, it's difficult for suturing tools to extend into the incision deeply enough to perform suturing. Therefore, there is an urgent needed to develop surgical devices that are suitable for assisting minimally invasive surgery.

SUMMARY OF THE INVENTION

Therefore, an object of the present invention is to provide a surgical guidewire device for assisting minimally invasive surgery.

According to the present invention, a surgical guidewire device includes an outer tube extending along an axial direction and a guide needle.

The outer tube is hollow and has a tube distal end, a tube proximal end and a needle tip formed at the tube distal end.

The guide needle is movably disposed in the outer tube and includes a needle proximal end and a needle eye structure being a hollow structure and formed at the needle proximal end.

The needle eye structure protrudes from the tube proximal end before utilizing of the surgical guidewire device in performance of a surgery.

When the surgical guidewire device is in use, a suture is passed through the needle eye structure. When the guide needle moves relatively toward the tube distal end and then away from the outer tube, the suture is carried through the outer tube along with the needle eye structure.

The surgical guidewire device further includes a guidewire block. The guidewire block has a fixing part detachably disposed at the tube proximal end or the guide needle and a guidewire part having a treading structure. When the guidewire block is engaged to the tube proximal end of the outer tube, at least a part of the guidewire part and the treading structure pass through the needle eye structure.

The present invention also provides a suture fixation system equipped with the surgical guidewire device for closing an interspace formed between wound sites.

The steps of using the suture fixation system include: piercing the wound sites on two sides of the interspace with the needle tip; placing a suture into the needle eye structure and moving the guide needle relative to the tube distal end to away from the outer tube thereby the suture penetrates through the outer tube; moving the outer tube relative to the interspace until the outer tube separated from the wound sites and interspace; and tying two ends of the suture to close the interspace.

The suture fixation system includes the surgical guidewire device and a thread hooking device.

The thread hooking device includes a handle part, a holding part and a long tubular part having two ends respectively connected to the handle part and a holding part.

The holding part has a hook element, a hook portion, a wire containing space and a closure element. The hook portion extends from an end of the hook element and curved inward toward the handle part. The wire containing space is defined between the hook element and the hook portion. The closure element is connected to the hook element and is movably relative to the hook portion to open or close the wire containing space.

When the suture fixation system is in use, the holding part is inserted into the incision and moves toward the outer tube. The suture is pulled by the thread hooking device, allowing the suture to penetrate the wound sites with the two ends of the suture exiting through the incision.

In the disclosure, the surgical guidewire device can assist in guiding the suture to a wound site located within the patient's body, such as a tendon rupture or ligament injuries, or to an area adjacent to the wound site, enabling the wound site to be sutured without creating a big incision.

DETAILED DESCRIPTION OF THE PREFERRED EMBODIMENTS

In order to make purposes, technical solutions, and advantages of the present invention to be clearer, the following content provides some preferred embodiments in accordance with the present invention.

Figure 1:
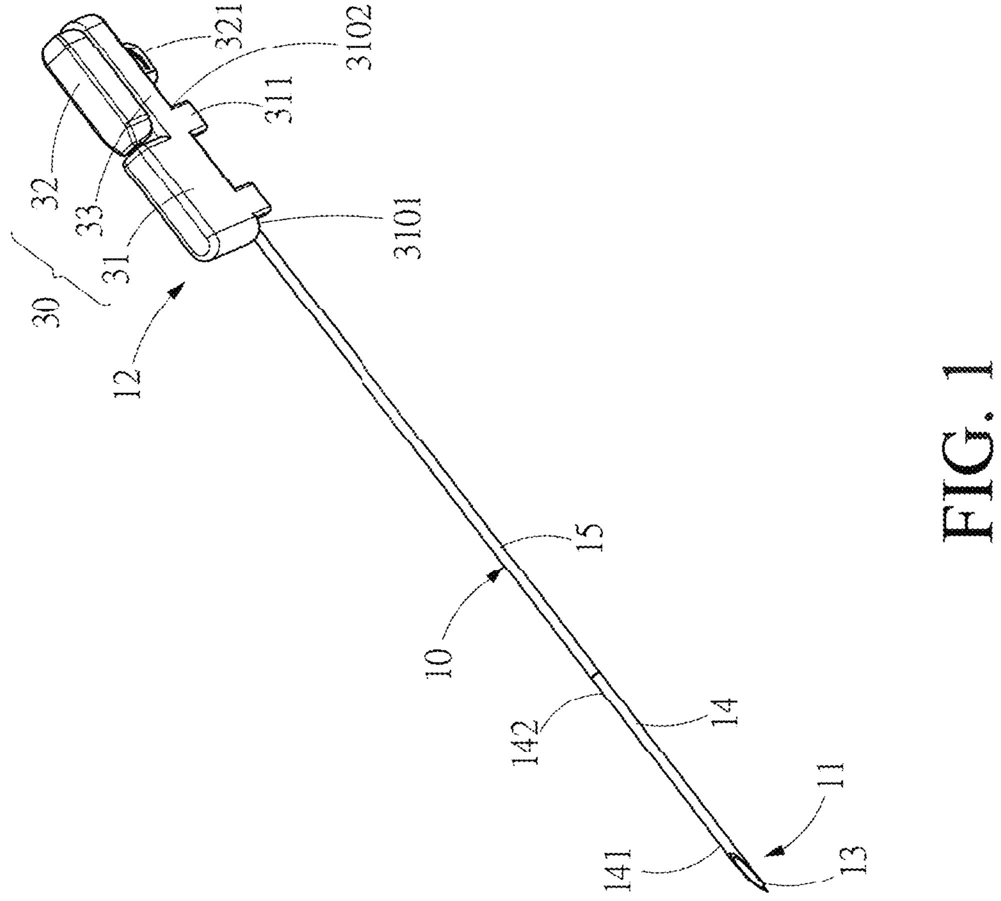
FIG. 1 is a perspective view illustrating a first preferred embodiment of a surgical guidewire device in accordance with the present invention.
Figure 2A:
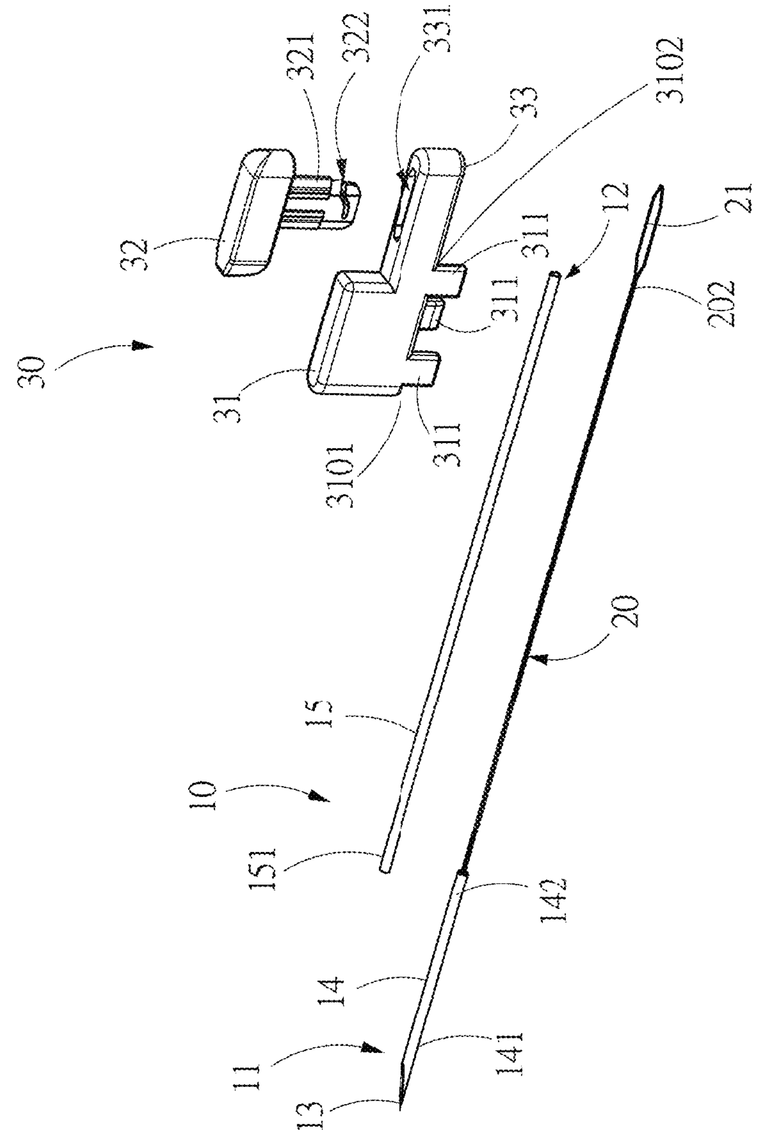
FIG. 2A is an exploded perspective view of the surgical guidewire device in FIG. 1.

Referring to FIG. 1 and FIG. 2A, a first preferred embodiment of a surgical guidewire device is disclosed. The surgical guidewire device includes an outer tube 10, a guide needle 20, and a guidewire block 30.

The outer tube 10 is a hollow tubular structure and extends along an axial direction. The outer tube 10 has a tube distal end 11, a tube proximal end 12 and a needle tip 13 formed at the tube distal end 11.

In another embodiment, the outer tube 10 is integrally formed and made of a metal material.

In this embodiment, the outer tube 10 includes a first outer tube portion 14 having a first distal end 141 and a first proximal end 142 and a second outer tube portion 15 having a second distal end 151. The first outer tube portion 14 is positioned at the second distal end 151, and the needle tip 13 is formed at a first distal end 141. The first proximal end 142 is detachably connected to the second distal end 151.

The guide needle 20 is movably disposed in the outer tube 10 and includes a needle proximal end 202 and a needle eye structure 21 being a hollow structure and formed at the needle proximal end 202.

Preferably, the guide needle 20 has flexibility and is capable of elastic deformation when subjected to be applied with an external force. An outer diameter of at least one part of the needle eye structure 21 is larger than a tube diameter of the outer tube 10 thereby the needle eye structure 21 can be allowed to remain outside of the tube proximal end 12 of the outer tube 10 while the guide needle 20 is disposed in the outer tube 10. When the guide needle 20 is moved relatively to the outer tube 10, the needle eye structure 21 can be elastically compressed by a pressure exerted by an inner wall of the outer tube 10, such that the needle eye structure 21 can enter the outer tube 10.

More preferably, the guide needle 20 is made of a metal material.

The guidewire block 30 includes a fixing part 31 and a guidewire part 32. The guidewire block 30 is detachably disposed at the tube proximal end 12 or the guide needle 20 by the fixing part 31.

The guidewire part 32 includes a treading structure 321. When the guidewire block 30 is engaged to the outer tube 10, at least one part of the treading structure 321 extends through the needle eye structure 21.

In this embodiment, the treading structure 321 extends along a radial direction. The guidewire part 32 is positioned at a fixing proximal end 3102 of the fixing part 31, and further includes a silt 322 formed in a free end of the treading structure 321. When the guidewire block 30 is engaged to the outer tube 10, at least one part of the treading structure 321 and the silt 322 extend through the needle eye structure 21.

The method of detachably disposing the fixing part 31 at the outer tube 10 is not limited, any technique that allows the fixing part 31 to be engaged to the outer tube 10 falls within the scope of the present invention.

Figure 2B:
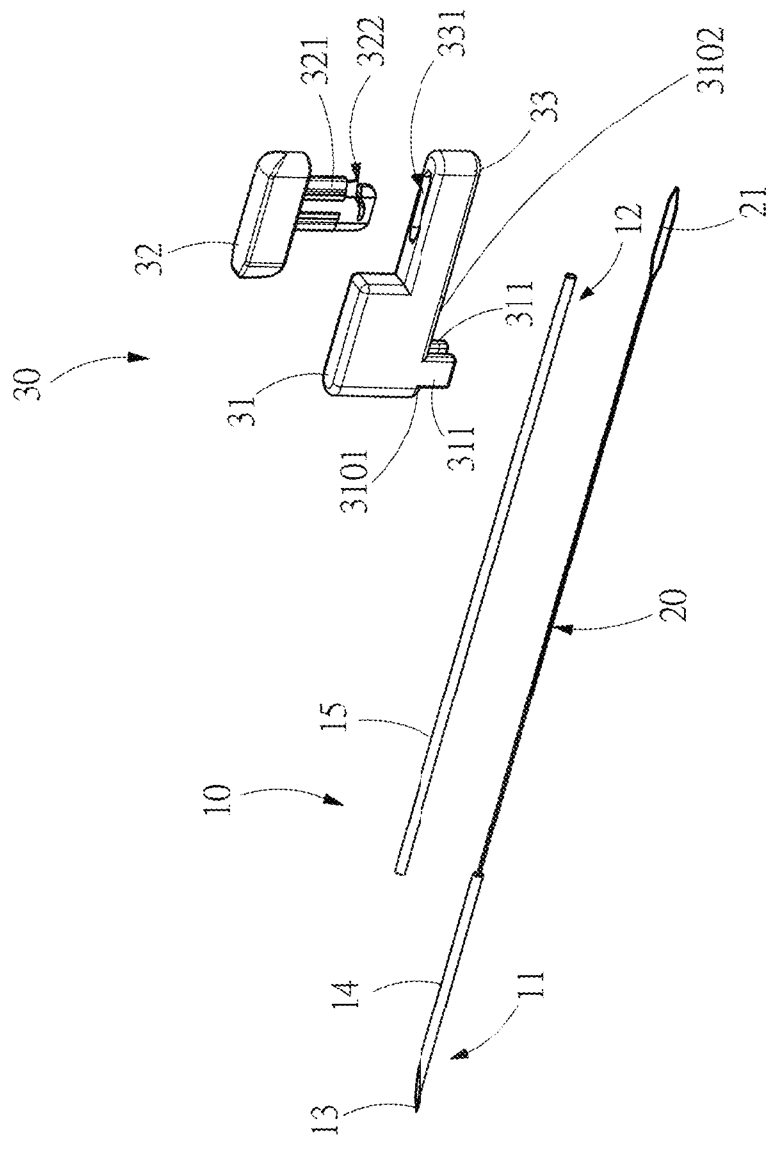
FIG. 2B is a perspective view illustrating another embodiment of a surgical guidewire device in accordance with the present invention.

Referring to FIG. 2B, in another embodiment, the fixing part 31 has a fixing distal end 3101, the fixing proximal end 3102 and two holding claws 311 extending from the fixing distal end 3101. The two holding claws 311 are radially spaced apart from each other and are enable to clamp opposite sides of the outer surface of the outer tube 10 to allow the outer tube 10 to be positioned between the two holding claws.

Referring to FIG. 1 and FIG. 2A again, in the first preferred embodiments, the fixing part 31 has three holding claws 311 extending from the fixing distal end 3101. The three holding claws 311 are staggered along the axial direction, with one of the three holding claws 311 positioned at a middle position is radially spaced apart from other two of the three holding claws 311. When the fixing part 31 is engaged to the outer tube, the one of the three holding claws 311 at the middle position and the other two of the three holding claws 311 clamp respectively the opposite sides of the outer surface of the outer tube 10. The axial staggered arrangement and the radial spaced arrangement of the three holding claws 311 improve the stability of engagement between the fixing part 31 and the outer tube 10.

In one embodiment, the fixing part 31 and the guidewire part 32 of the guidewire block 30 are formed as two detachably engaged blocks.

In this embodiment, the guidewire block 30 further includes an engaging part 33 extending from the fixing proximal end 3102. The engaging part 33 has an engaging hole 331 formed through the engaging part 33 and corresponding in a shape to at least part of an outer surface of the treading structure 321. The guidewire part 32 is engaged to the fixing part 31 with the treading structure 321 extending through the engaging hole 331. When the guidewire block 30 is engaged to the outer tube 10, the free end of the treading structure 321 extends and protrudes from the engaging hole 331 and the slit 322 extends through the needle eye structure 21.

Referring to FIG. 3A, FIG. 3B, FIG. 4A and FIG. 4B, the second and third preferred embodiments of a surgical guidewire device are disclosed.

In these embodiments, the guidewire block 30 is an elastic element with a U-shaped structure and is formed by bending a rigid wiring material. The guidewire block 30 includes a curved portion 34 and two wire end sections 35 extending from two ends of the curved portion 34 respectively. When applying pressure to the two ends of the curved portion 34, a width of the guidewire block 30 can be changed.

Figure 3A:
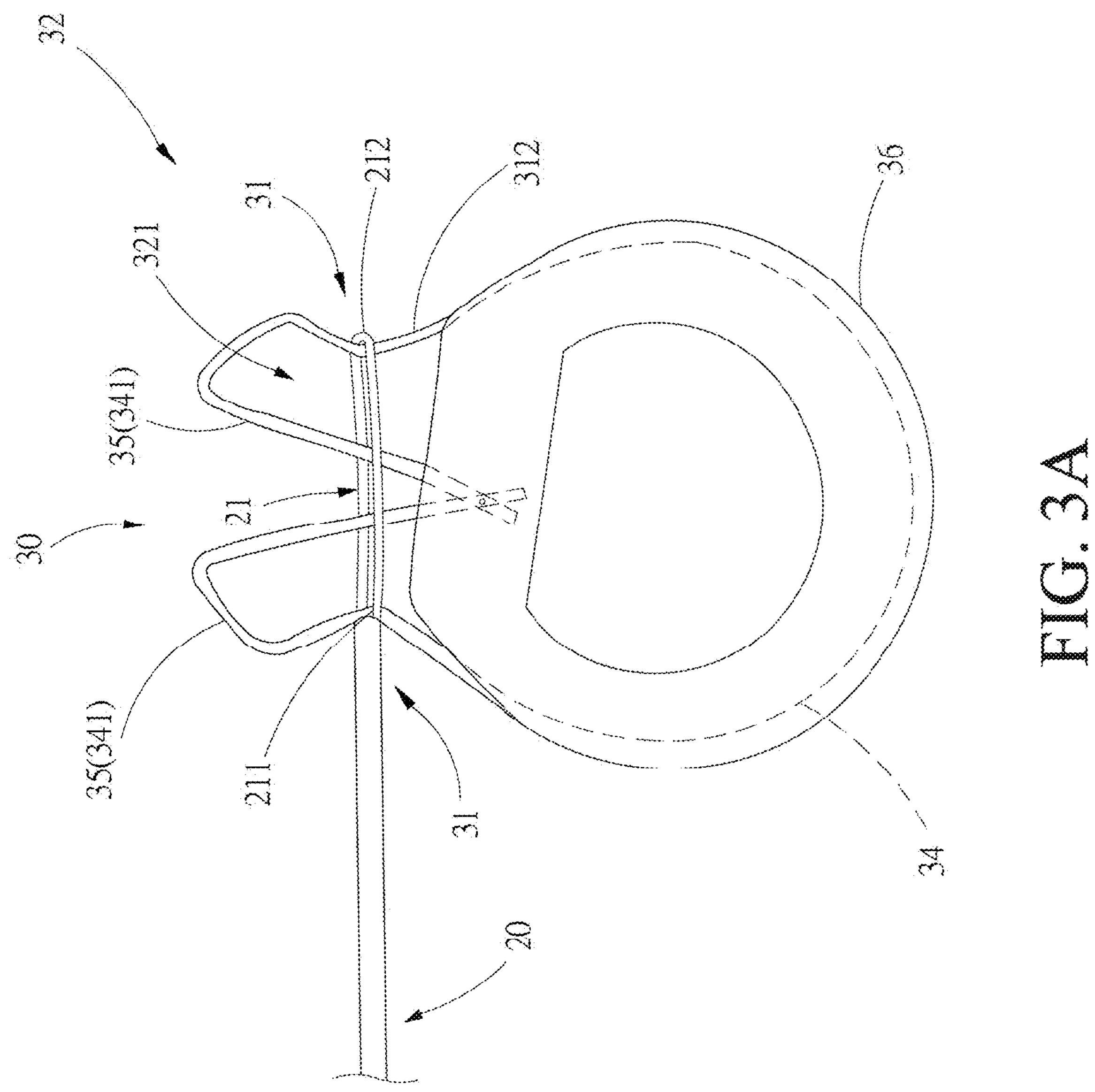
FIG. 3A and FIG. 3B illustrate side views of a second preferred embodiment of a surgical guidewire device in accordance with the present invention.
Figure 3B:
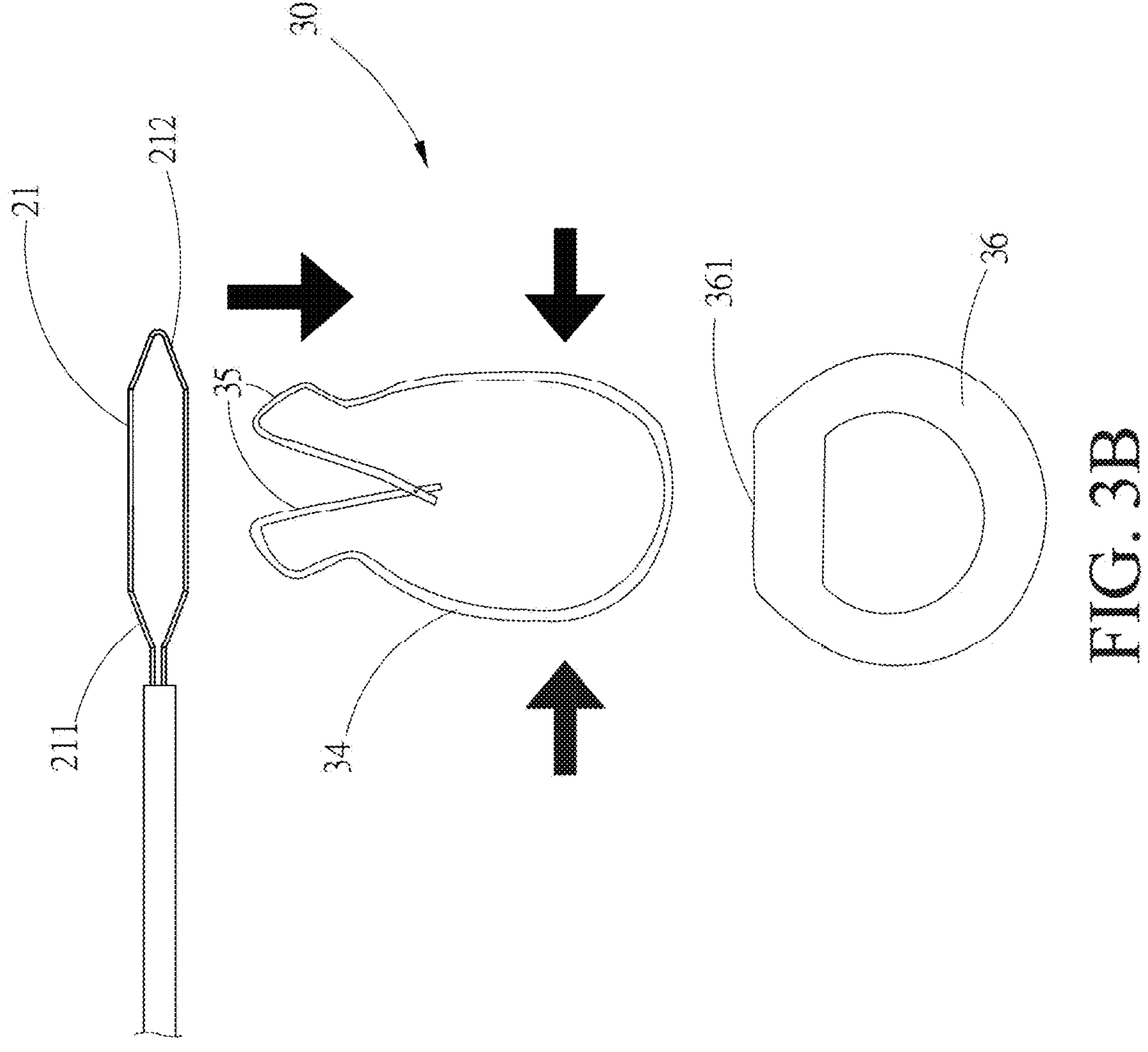

Referring to FIG. 3A and FIG. 3B, in the second preferred embodiment, the guidewire block 30 includes two fixing parts 31 respectively formed at two connections between the two ends of the curved portion 34 and the two wire end sections 35. A distance between the two fixing parts 31 is smaller than a width of any portion of the curved portion 34. A neck structure 312 is defined by the two fixing parts 31.

When the guidewire block 30 is engaged to the guide needle 20, a portion of the guidewire block 30 extends through the needle eye structure 21, consequently, the two wire end sections 35 extend through the needle eye structure 21 and are defined as the guidewire part 32 on one side of the needle eye structure 21, and the two fixing parts 31 are positioned within the needle eye structure 21. The two fixing parts 31 respectively abut against a needle-eye distal 211 end and a needle-eye proximal end 212 of the needle eye structure 21, continuously providing a biasing force toward the needle eye structure 21, thereby the guidewire block 30 can be securely engaged within the needle eye structure 21 via the neck structure 312 formed by the two fixing parts 31.

In this situation, the guidewire part 32 is formed on one side of the neck structure 312, a maximum width of the threading structure 321 is smaller than a maximum width of the curved portion 34 remaining on the other side of the needle eye structure 21.

The guidewire block 30 can be removed from the needle eye structure 21 by applying pressure to the two ends of the curved portion 34 to reduce a maximum width of the guidewire part 32 to be smaller than the distance between the needle-eye distal 211 end and the needle-eye proximal end 212.

In the second preferred embodiment, the maximum width of the curved portion 34 of the guidewire block 30 is larger than a maximum width of the two wire end sections 35. At least one of the wire end sections 35 is further bent to form a sub curved portion 341, which creates a perforation that serves as the threading structure 321.

Figure 4A:
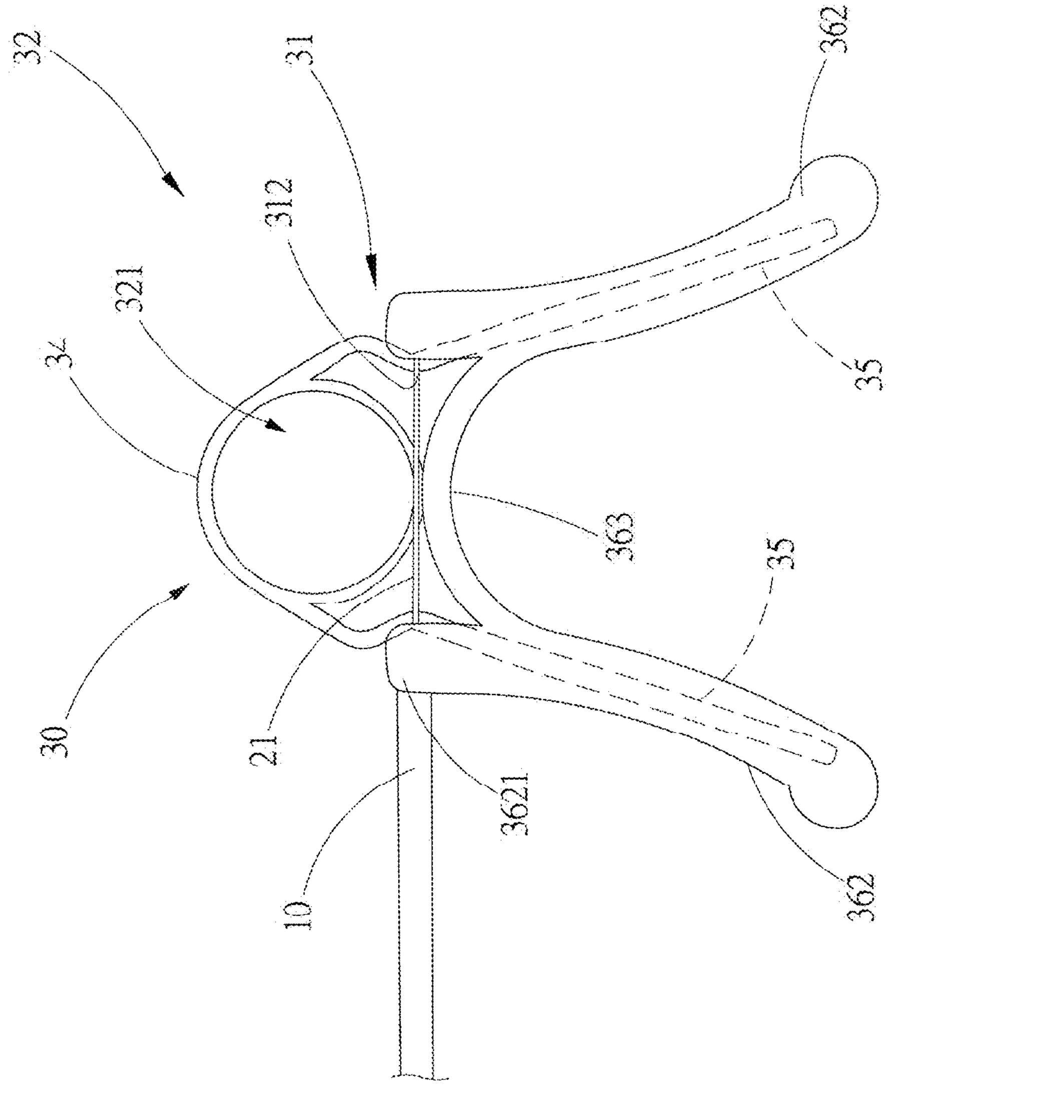
FIG. 4A and FIG. 4B illustrate side views of a third preferred embodiment of a surgical guidewire device in accordance with the present invention.

As shown in FIG. 4A, the maximum width of the curved portion 34 of the guidewire block 30 is smaller than the maximum width of the two wire end sections 35, and a perforation defined by the curved portion 34 directly serves as the threading structure 321.

Referring to FIG. 3A and FIG. 3B again, additionally, the guidewire block 30 further includes a handle assembly 36 positioned on the side of needle eye structure 21 opposite the threading structure 321. The handle assembly 36 is designed to prevent operational errors by distinguishing the threading structure 321 from the curved portion 34.

In the second preferred embodiment shown in FIG. 3A and FIG. 3B, the handle assembly 36 is a hollow annular structure configured to house the curved portion 34. The handle assembly 36 includes a handle opening 361 disposed through an outer wall of the handle assembly 36 and aligned with the two fixing parts 31. The two wire end sections 35 are respectively bent toward the handle opening 361 to form two sub curved portions 341, which serve as two threading structures 321.

Figure 4B:
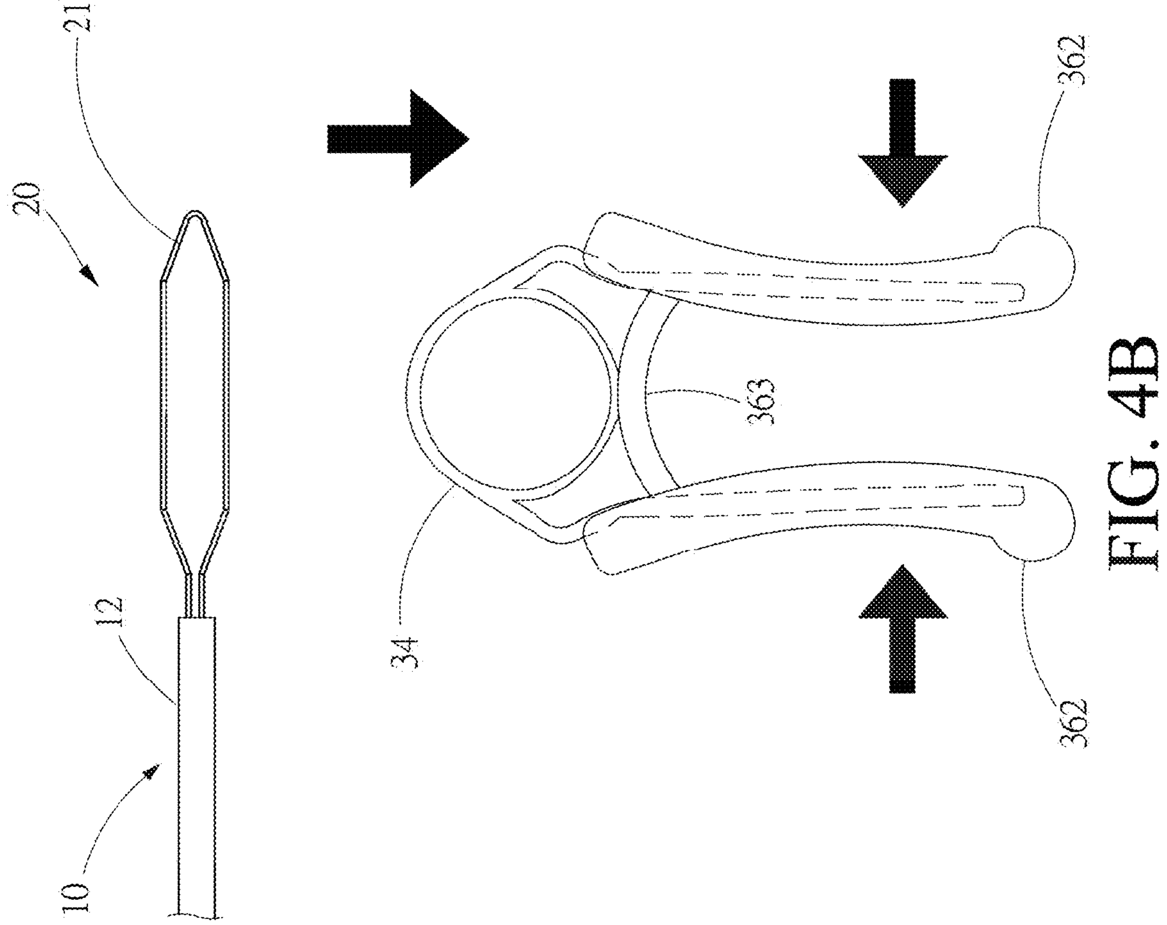
Figure 4C:
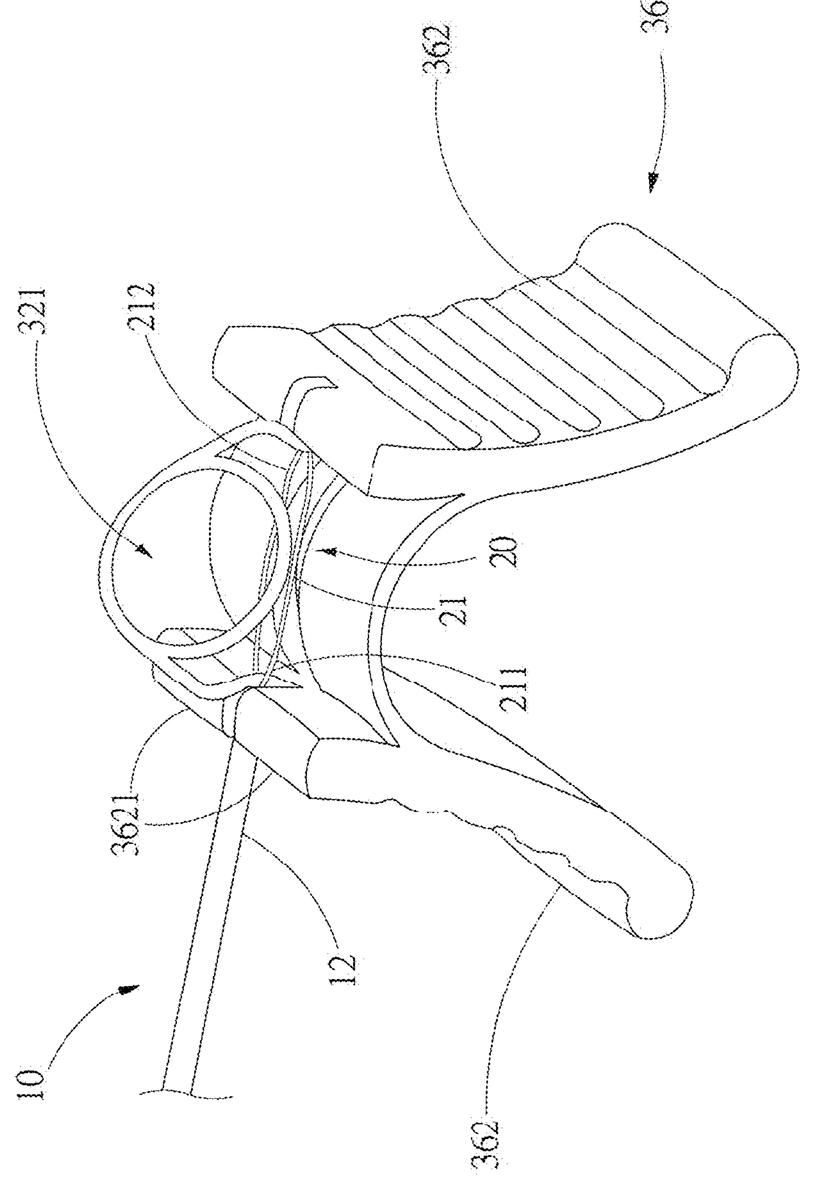
FIG. 4C is a perspective view illustrating of the surgical guidewire device in FIG. 4A.

In the third preferred embodiment shown in FIG. 4A, FIG. 4B and FIG. 4C, the handle assembly 36 includes two handle bars 362 and a deforming member 363 connected between the two handle bars 362. The two handle bars 362 are configured to accommodate the two wire end sections 35 respectively. When pressure is applied to the handle assembly 36 to move the two handle bars 362 toward each other, the deforming member 363 is deformed elastically.

Preferably, the one of the two handle bars 362 adjacent to the outer tube 10 includes two holding elements 3621 enabling the tube proximal end 12 of the outer tube 10 to be positioned between the two holding elements 3621, thereby a connection of the handle assembly 36 with the outer tube 10 and the guide needle 20 is enhanced.

The surgical guidewire device provided by the present invention facilitates guiding a suture to a wound site located either inside or outside the body, such as tendon or ligament ruptures, or to an area adjacent to the wound site, thereby an interspace formed at the wound site is sutured to close without a large incision.

Referring to FIG. 5A to FIG. 5E, an operational process for the use of the surgical guidewire device shown in FIG. 1 is disclosed. The surgical guidewire device is configured as part of a suture fixation system. In this process, a wound site B may be an incision on a body surface to be sutured, and an interspace D is formed within the incision.

Figure 5A:
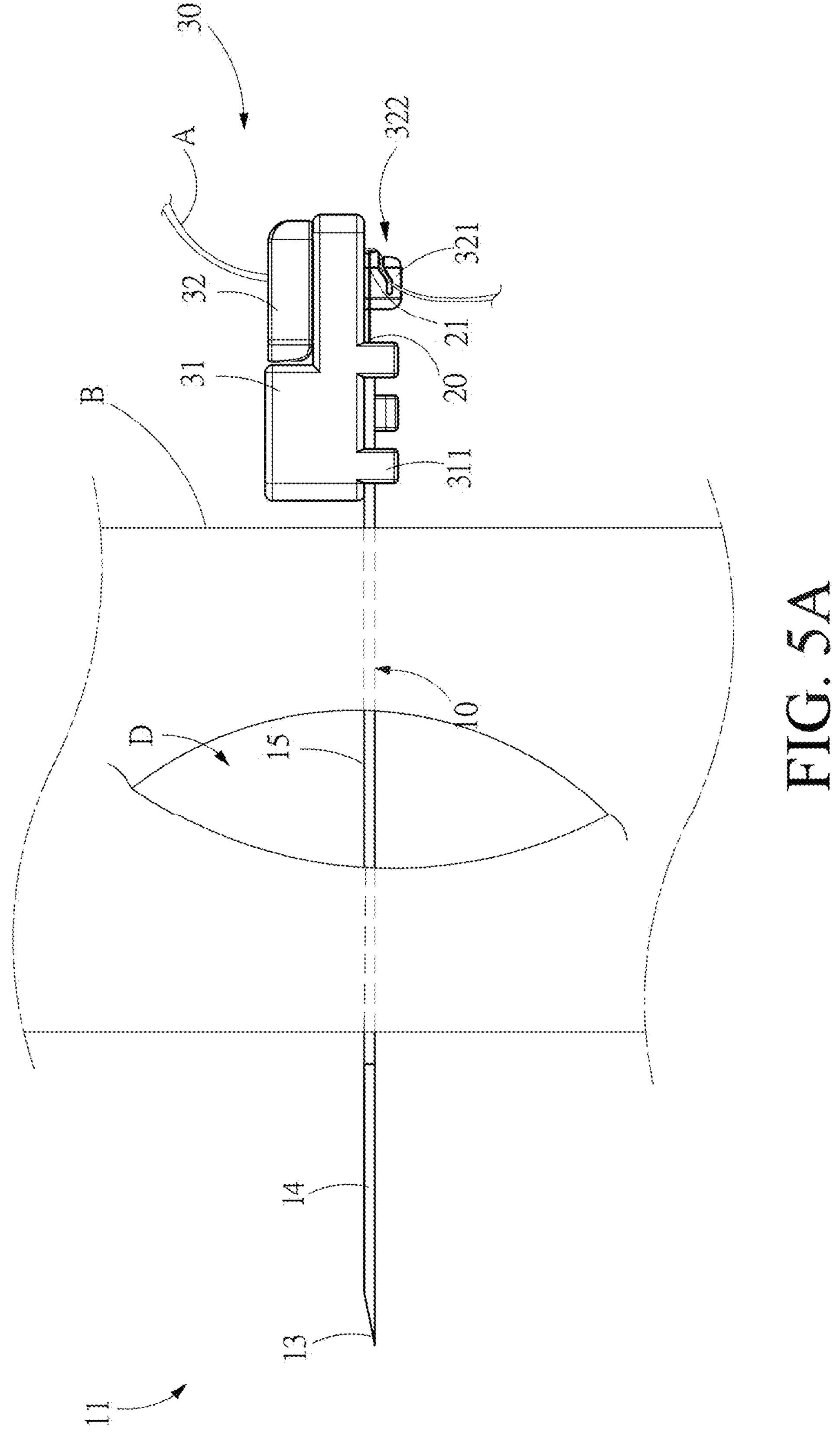
FIG. 5A to FIG. 5E illustrate operational side views for showing steps of using the surgical guidewire device in FIG. 1.

FIG. 5A is shown the surgical guidewire device in an assembled state prior to guiding a suture A, while the outer tube 10, the guide needle 20, and the guidewire block 30 are engaged to each other. When the surgical guidewire device is in use, the needle tip 13 is used to pierce through tissues on both sides of the wound site B to be sutured. The suture A is then placed into the threading structure 322.

Figure 5B:
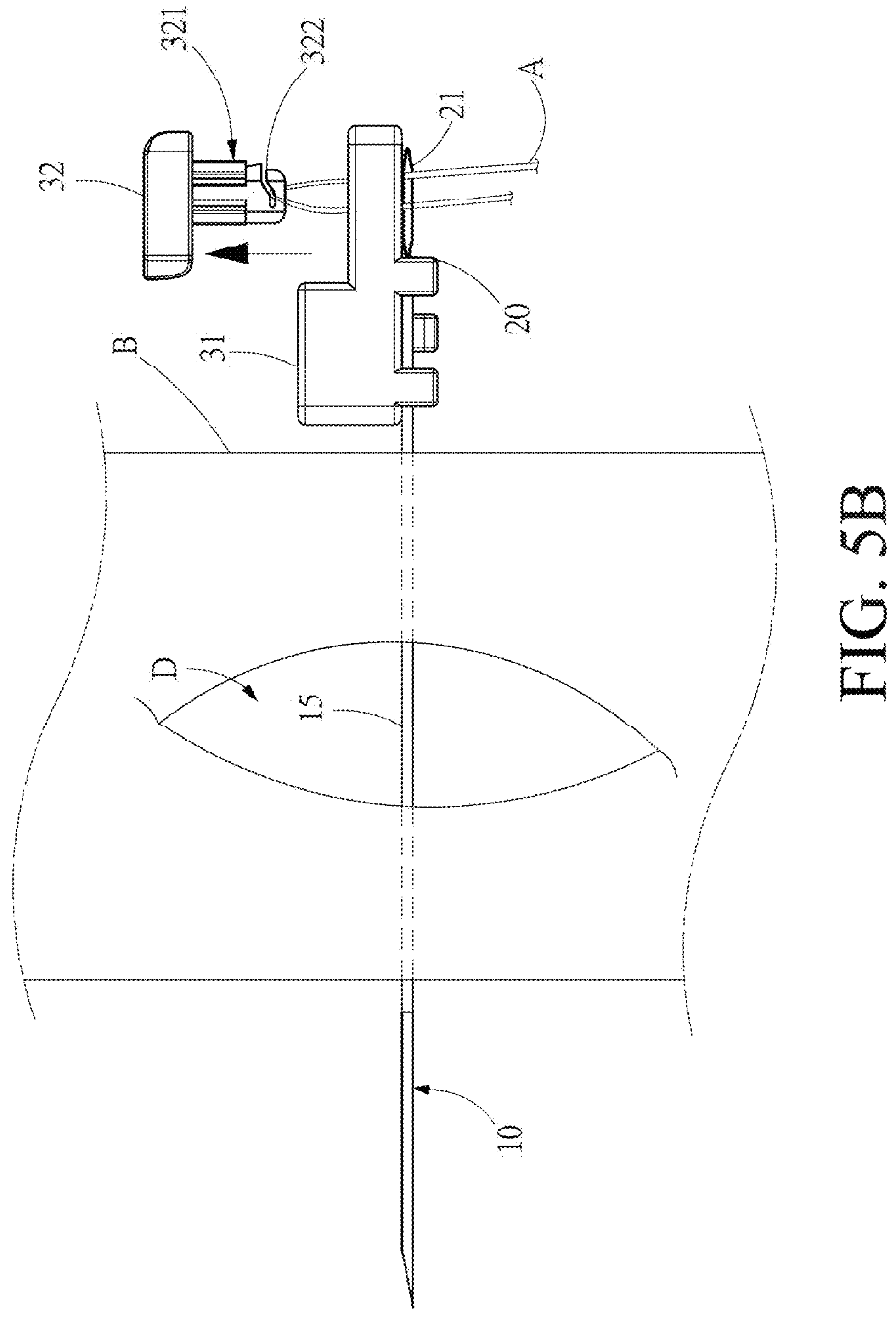

As shown in FIG. 5B, the guidewire part 32 is subsequently moved out of the needle eye structure 21 to make the suture Abe carried through the needle eye structure 21 with the threading structure 321.

In one embodiment, the fixing part 31 and the guidewire part 32 are integrally formed, this step of extending the suture A through the threading structure 321 may involve detaching the guidewire block 30 from either the outer tube 10 or the needle eye structure 21.

Figure 5C:
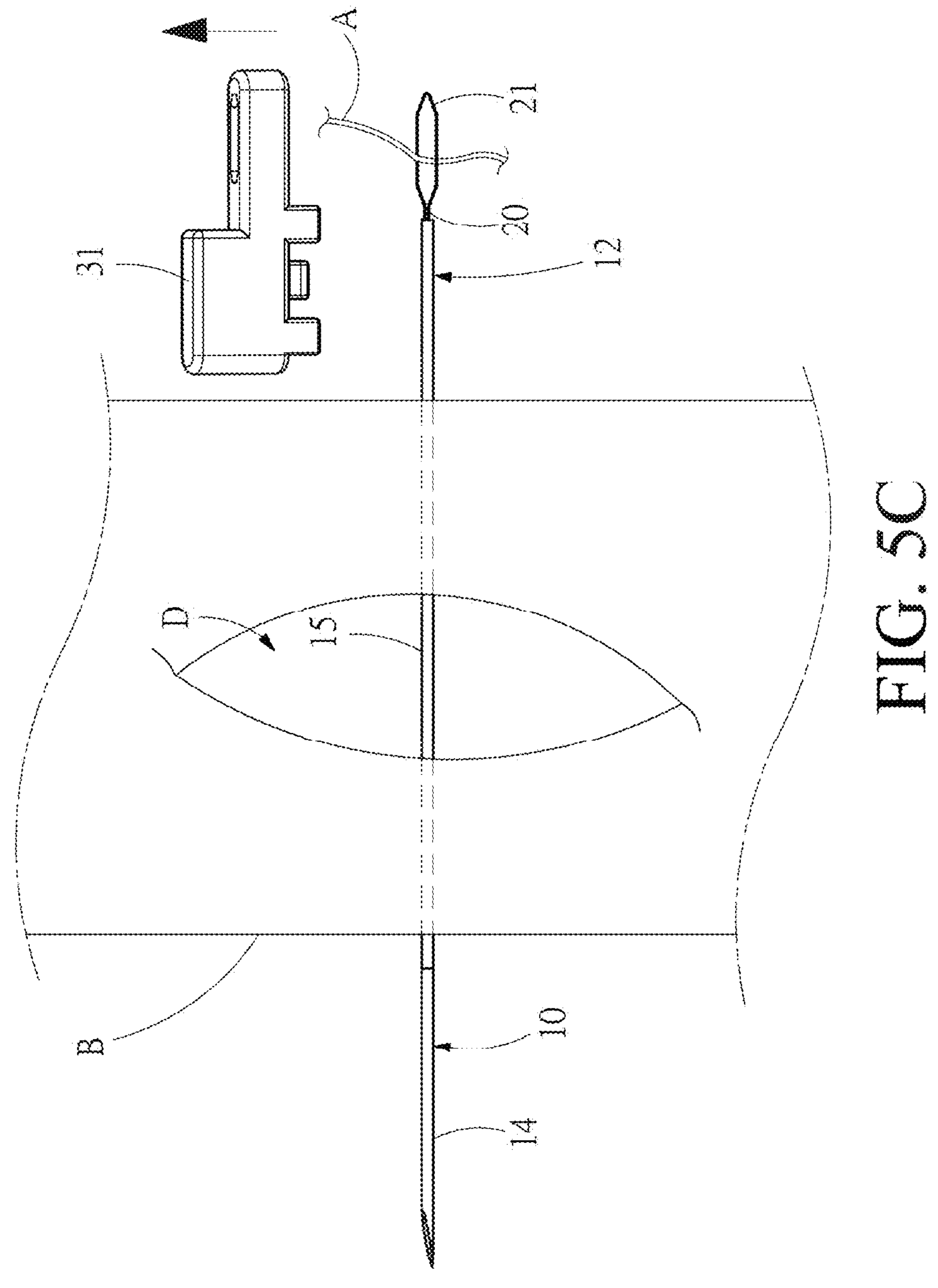

As shown in FIG. 5C, the fixing part 31 can optionally be detached from the outer tube 10. Alternatively, the fixing part 31 may remain on the outer tube 10, providing a gripping area during use. Additionally, the fixing part 31 can be served as a securing point for positioning devices, such as a locating frame or clamper to secure a relative position between the surgical guidewire device and the wound site B, so that unintended contact with the needle eye structure 21 or movement of the outer tube 10 through the wound site B can be prevented.

Notably, the design of the threading structure 321 (as shown in FIG. 5B) extending through the needle eye structure 21 not only assists in threading the suture A through the needle eye structure 21 but also ensures that the needle eye structure 21 remains positioned outside the tube proximal end 12 of the outer tube 10, consequently, unintended contact can be prevented to cause the needle eye structure 21 displacing into the outer tube 10 and to facilitate ease of use of the surgical guidewire device.

Figure 5D:
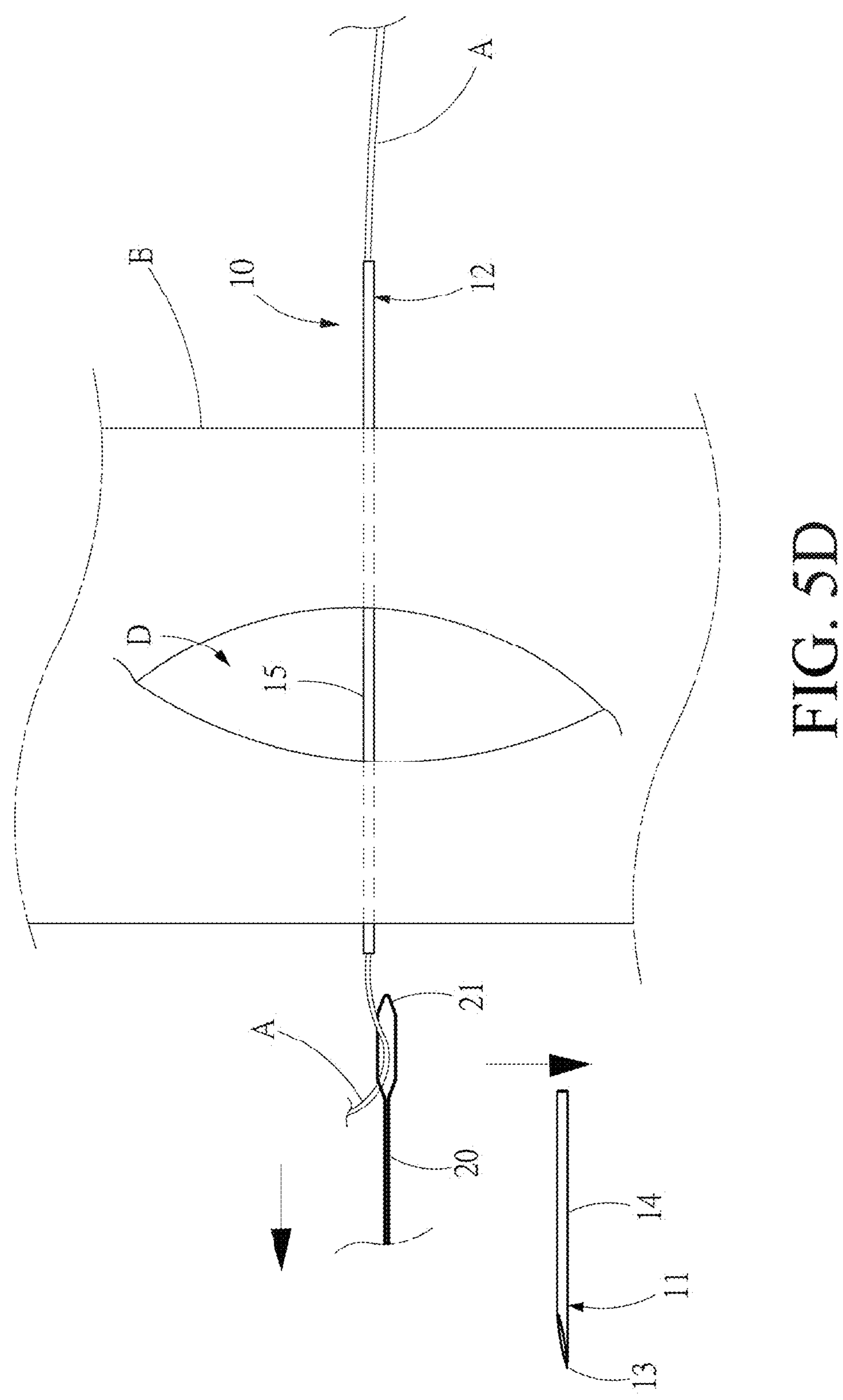

As shown in FIG. 5D, the guide needle 20 is moved relative to the outer tube 10 toward the tube distal end 11 until the guide needle 20 exits the outer tube 10 from the tube distal end 11. At this point, the suture A is moved along with the needle eye structure 21 and passes through the outer tube 10 in the axial direction. Notably, as the needle eye structure 21 moves within the outer tube 10, pressure exerted by the inner wall of the outer tube 10 elastically compresses the needle eye structure 21, helps the needle eye structure 21 securely grip the suture A during movement and preventing the suture A from slipping out.

Figure 5E:
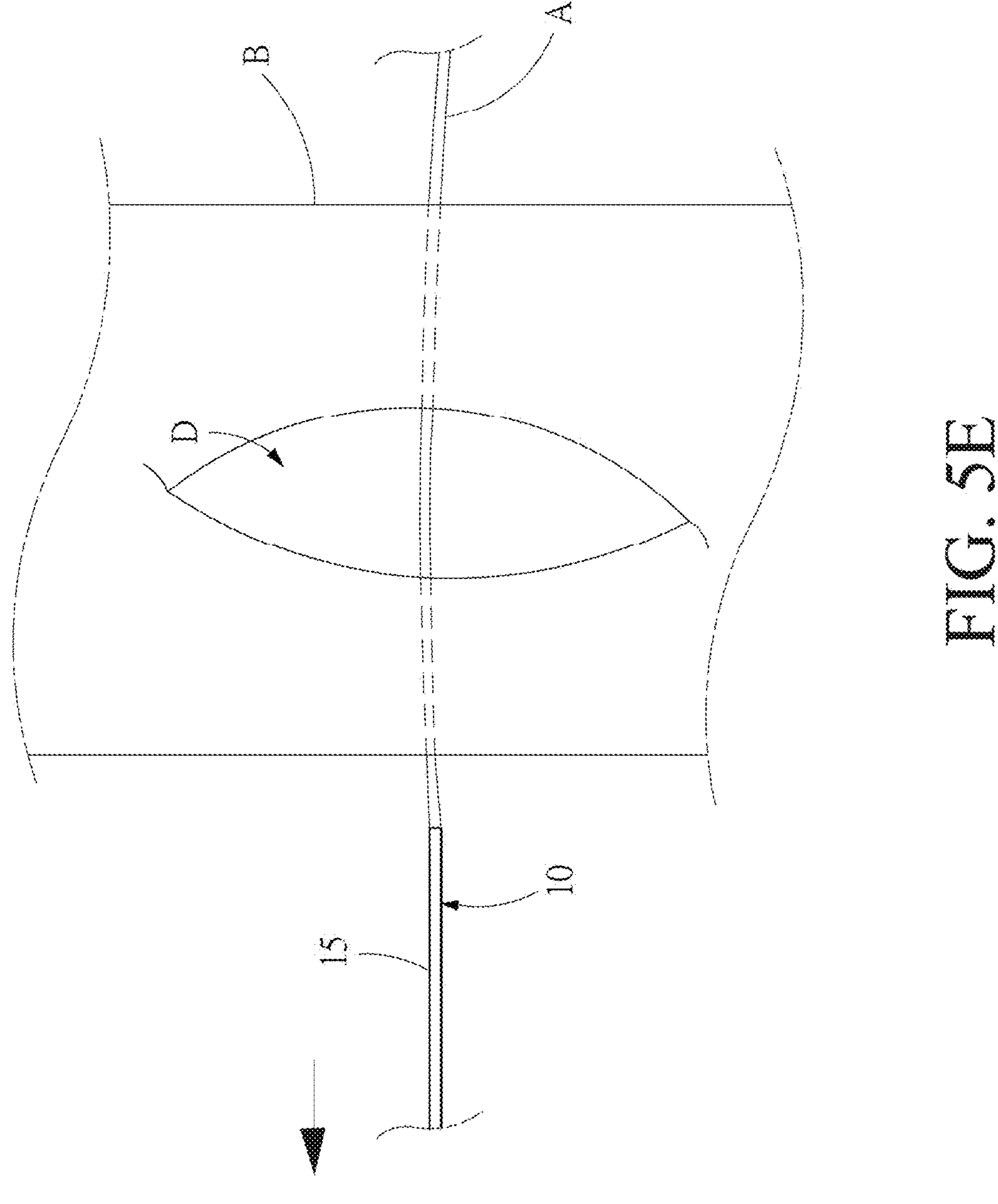

In one embodiment, the outer tube 10 comprises the first outer tube portion 14 and the second outer tube portion 15 that are engaged to each other, the first outer tube portion 14 can be detached from the second outer tube portion 15 when the outer tube 10 pierces the tissues on both sides of the wound site B to make the first outer tube portion 14 protruding through the tissue on one side of the wound site B. In this way, a travel distance required for the guide needle 20 to move toward the tube distal end 11 is reduced so as to facilitate a guidance of the suture A through the outer tube 10, as shown in FIG. 5E.

Finally, the outer tube 10 or the second outer tube portion 15 is moved along the axial direction relative to the wound site B until the outer tube 10 or the second outer tube portion 15 is removed from the wound site B. The process of guiding the suture A through the interspace D and leaving the suture A positioned between the both sides of the wound site B is completed. Furthermore, depending on the size of the interspace D, the number of sutures A guided to pass through the tissues on the both sides of the wound site B can be changed. Subsequently, two ends of each suture A can be tied together to achieve the closure of the interspace D.

Figure 6A:
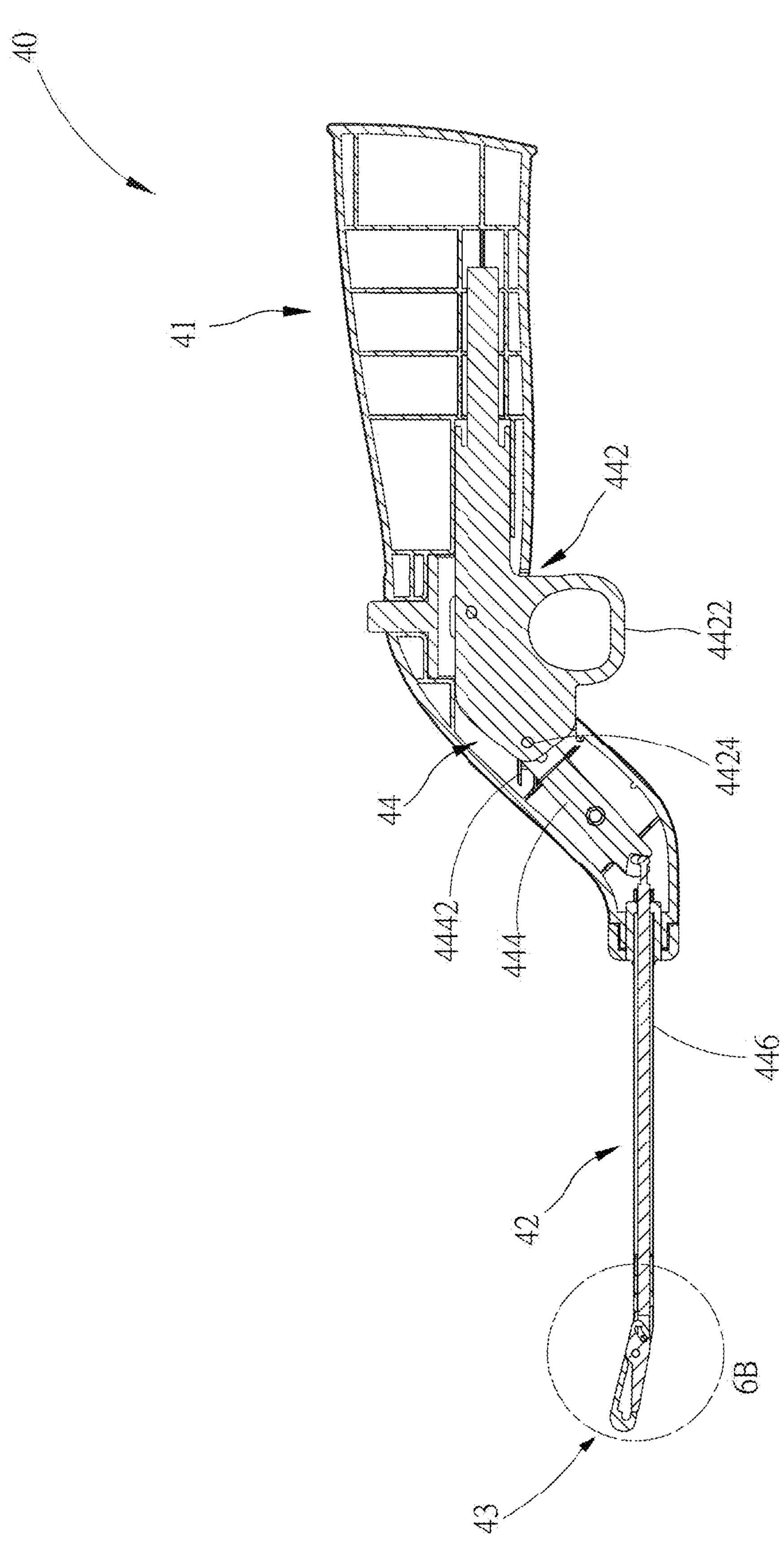
FIG. 6A to FIG. 6D illustrate cross sectional side views of a fourth preferred embodiment of a thread hooking device of a suture fixation system in accordance with the present invention.
Figure 6B:
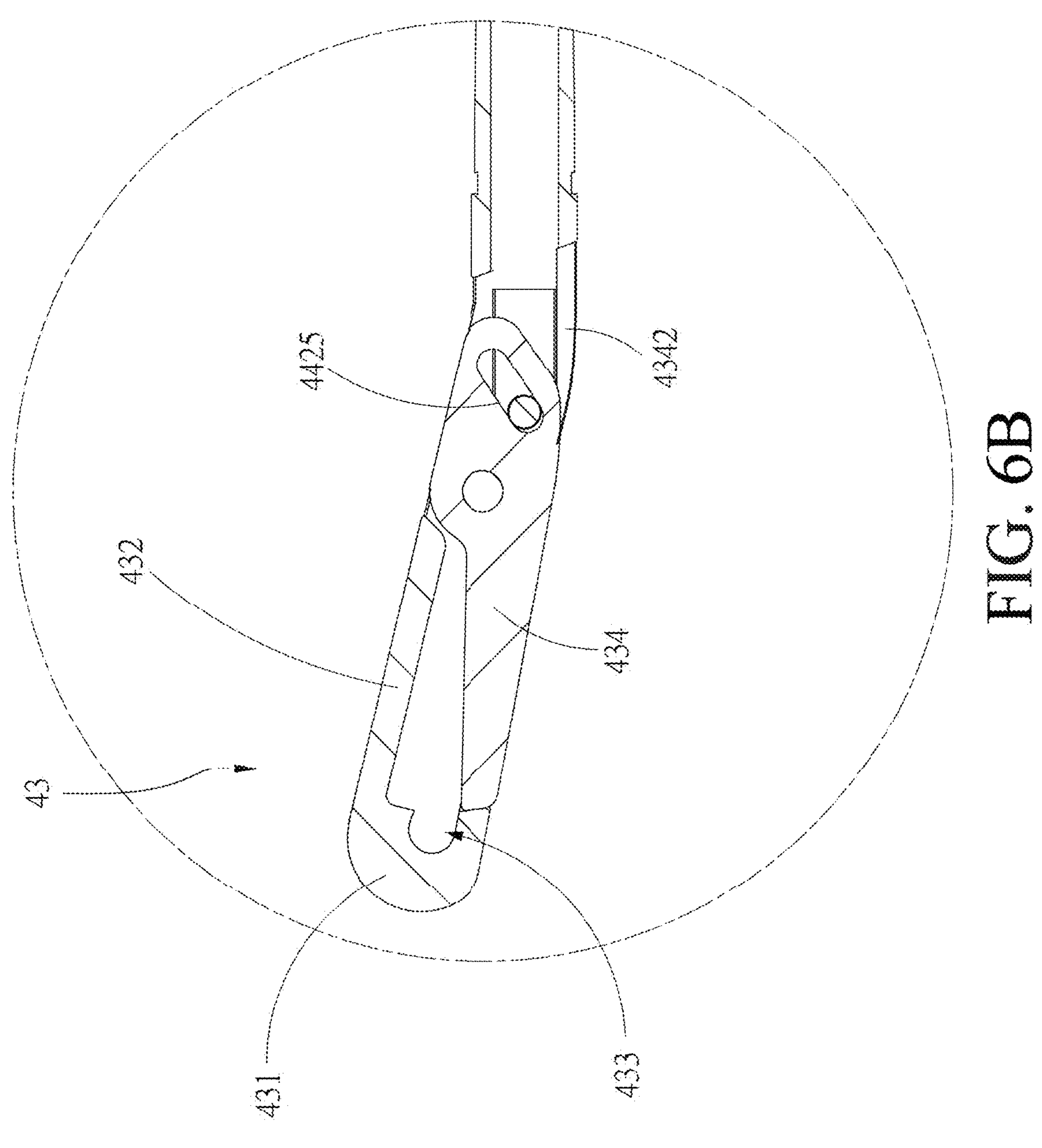

Referring to FIG. 8A to FIG. 8E, an operational process for the use of a fourth preferred embodiment of a suture fixation system shown in FIGS. 6A and 6B is disclosed. The suture fixation system is used for closing an interspace D formed between two wound sites B, such as wound sites occurring after a tendon or ligament rupture within the body, wherein an incision B1 is formed on body surface between the two wound sites B.

The fourth preferred embodiment of the suture fixation system includes the surgical guidewire device and a thread hooking device 40.

Figure 6C:
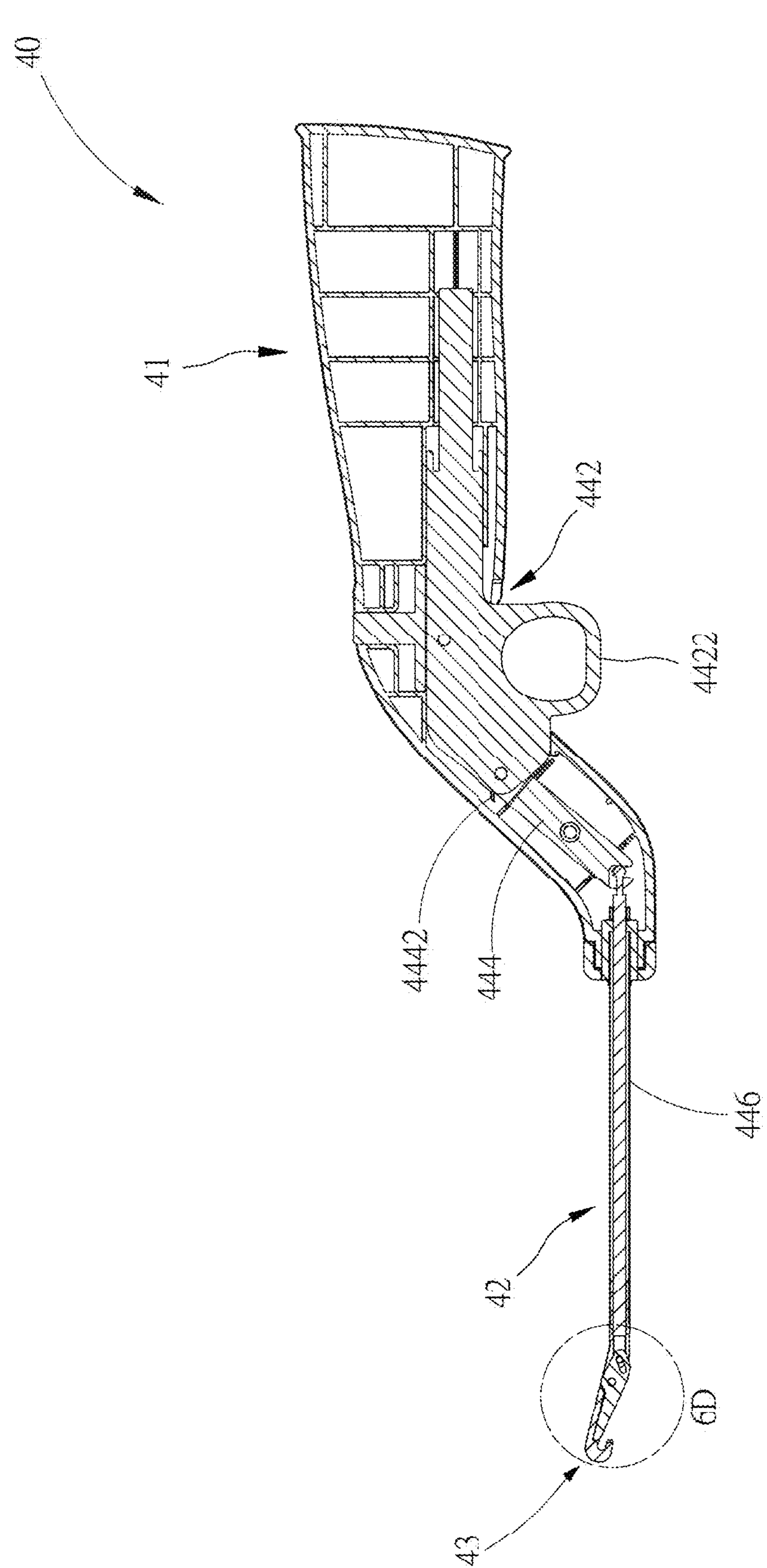
Figure 6D:
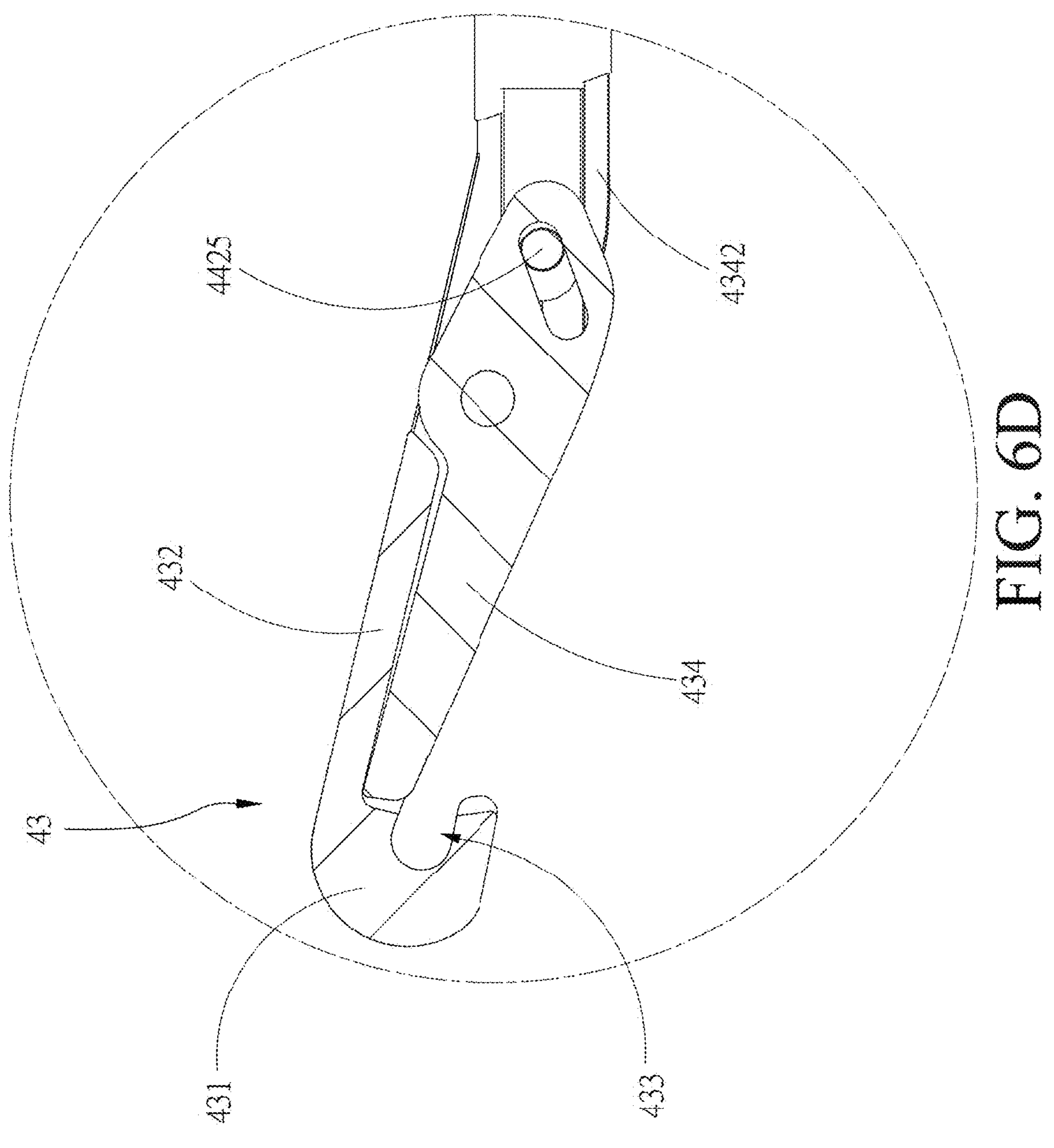

As shown in FIG. 6A to FIG. 6D, in the fourth preferred embodiment, the thread hooking device 40 includes a handle part 41, a long tubular part 42, and a holding part 43. The handle part 41 is provided for gripping by a user. The long tubular part 42 has two ends respectively connected to the handle part 41 and the holding part 43. The holding part 43 includes a hook element 432, a hook portion 431, a wire containing space 433 and a closure element 434. The hook portion 431 extends from an end of the hook element 432 and is curved inward toward the handle part 41. The wire containing space 433 is formed between the hook portion 431 and the hook element 432. The closure element 434 is movably displaced relative to the hook element 432 to open (as shown in FIGS. 6C and 6D) or close (as shown in FIGS. 6A and 6B) the wire containing space 433.

With reference to FIG. 5A to FIG. 5D and FIG. 8A to FIG. 8D, in this embodiment, when the surgical guidewire device is in used, the needle tip 13 is used to pierce one of the wound sites B through the body surface, and the guide needle 20 is moved out relative to the outer tube 10 and guides the suture A to penetrate into the outer tube 10. At this stage, the holding part 43 of the thread hooking device 40 is inserted into the body through the incision B1. The thread hooking device 40 is then moved toward the outer tube 10 to allow the hook element 432 to engage with the outer tube 10, and to position the outer tube 10 within the wire containing space 433.

Next, the outer tube 10 is moved relative to the wound site B being pierced and opposite to the thread hooking device 40 until the outer tube 10 is detached from the wound site B. During a movement of the outer tube 10, the user can tactilely sense a moment when the outer tube 10 moves relative to the hook element 432 and exits from the wire containing space 433. At this point, the suture A remains positioned within the wire containing space 433, and a first suture end A01 of the suture A can be pulled by the thread hooking device 40 toward the incision B1 and then away from the incision B1, thereby a distribution path of the suture A within the body is changed.

Figure 8A:
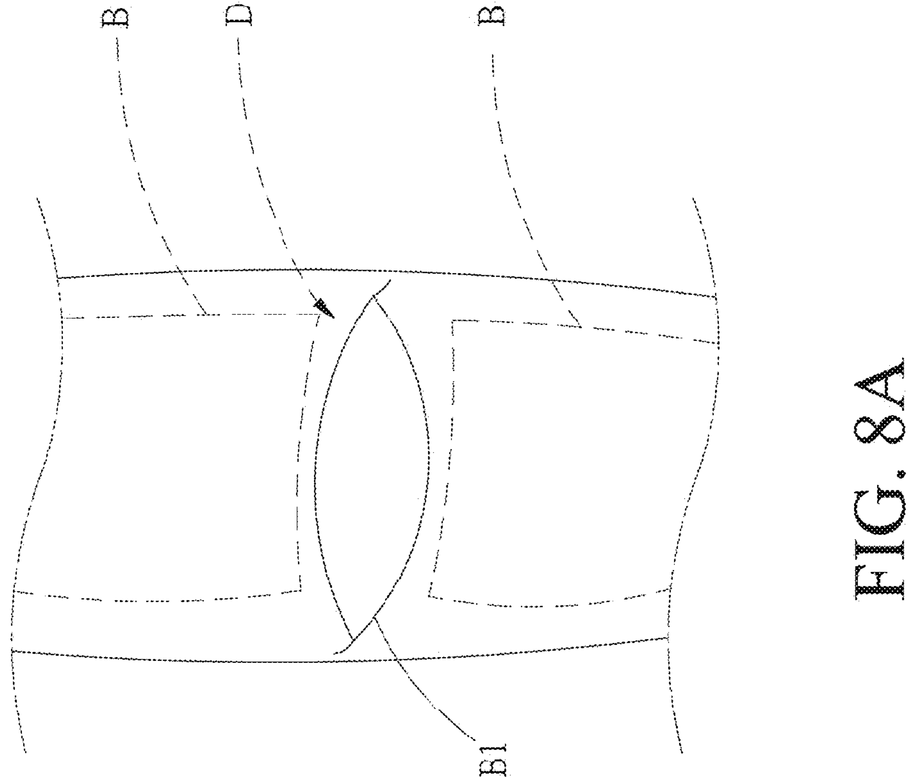
FIG. 8A to FIG. 8G illustrate operational side views for showing steps of using the suture fixation system in FIG. 6A.
Figure 8B:
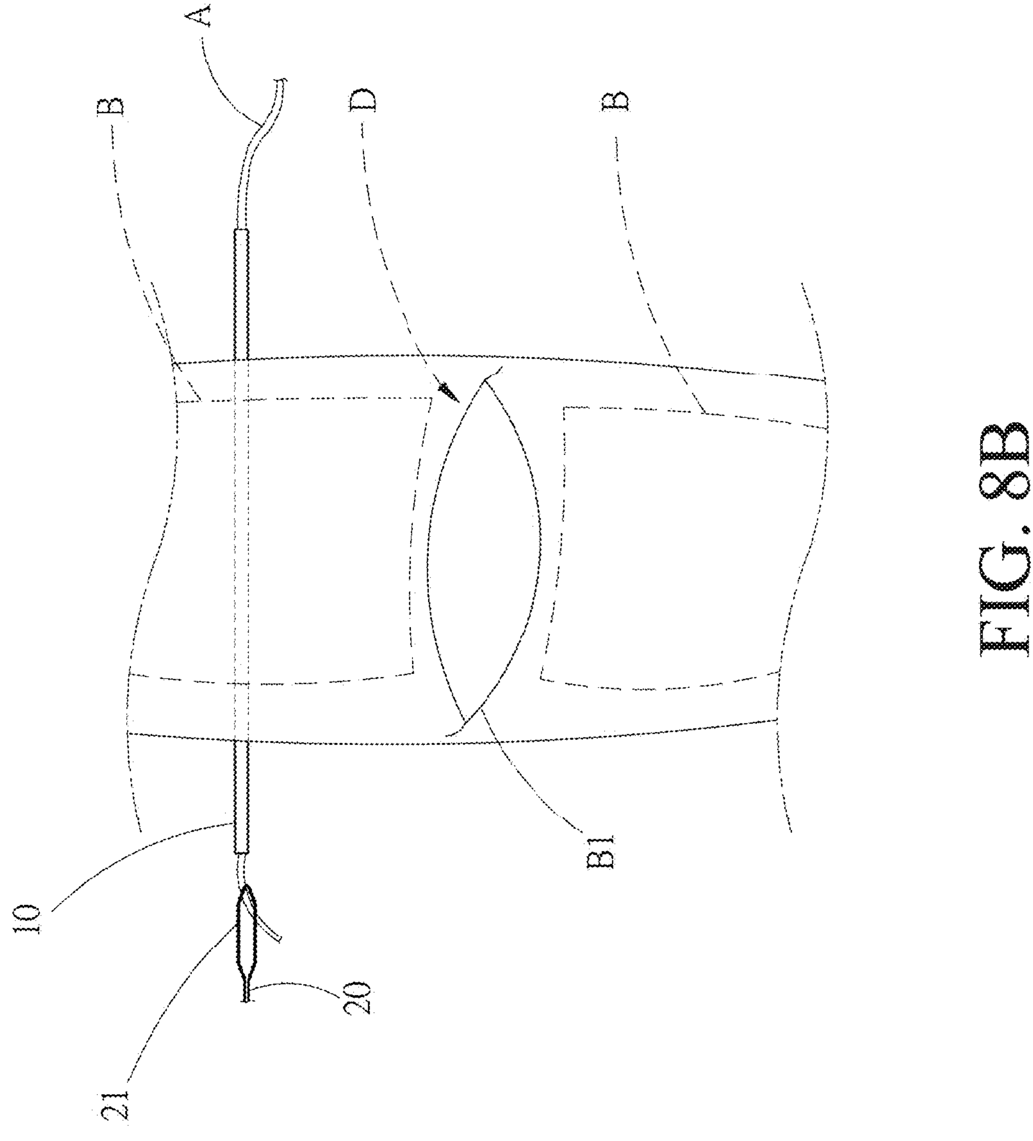
Figure 8C:
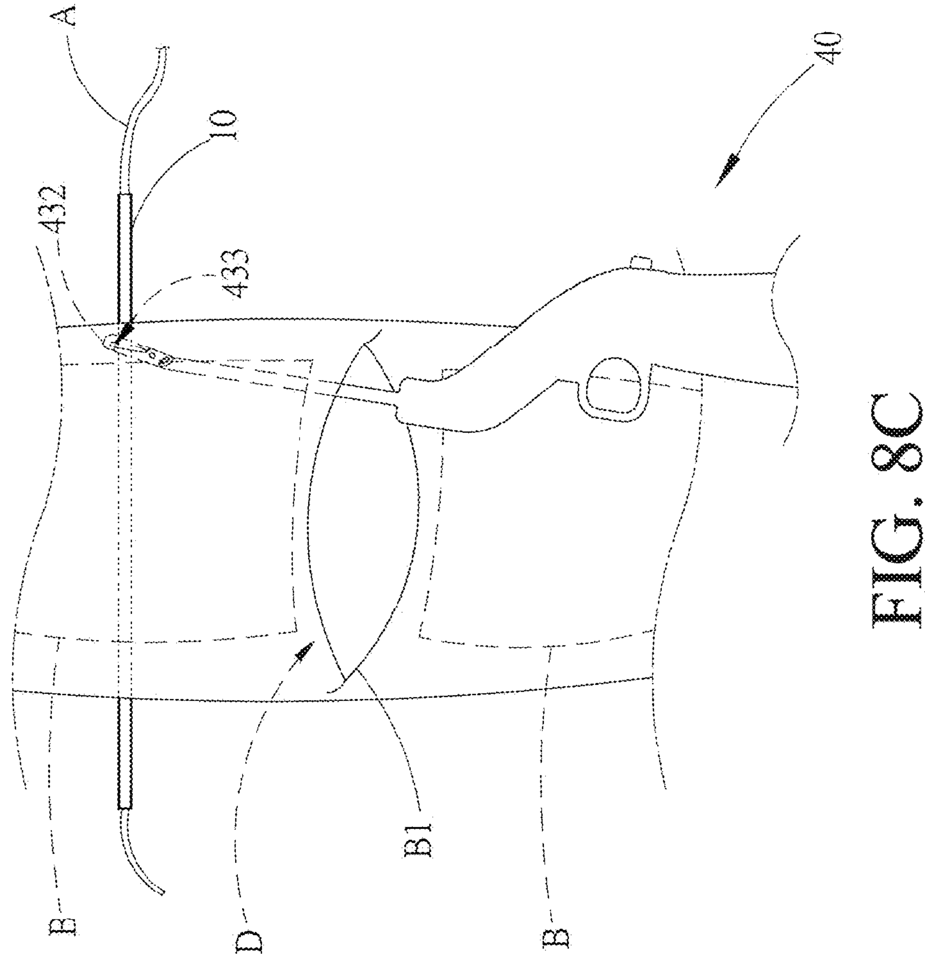
Figure 8D:
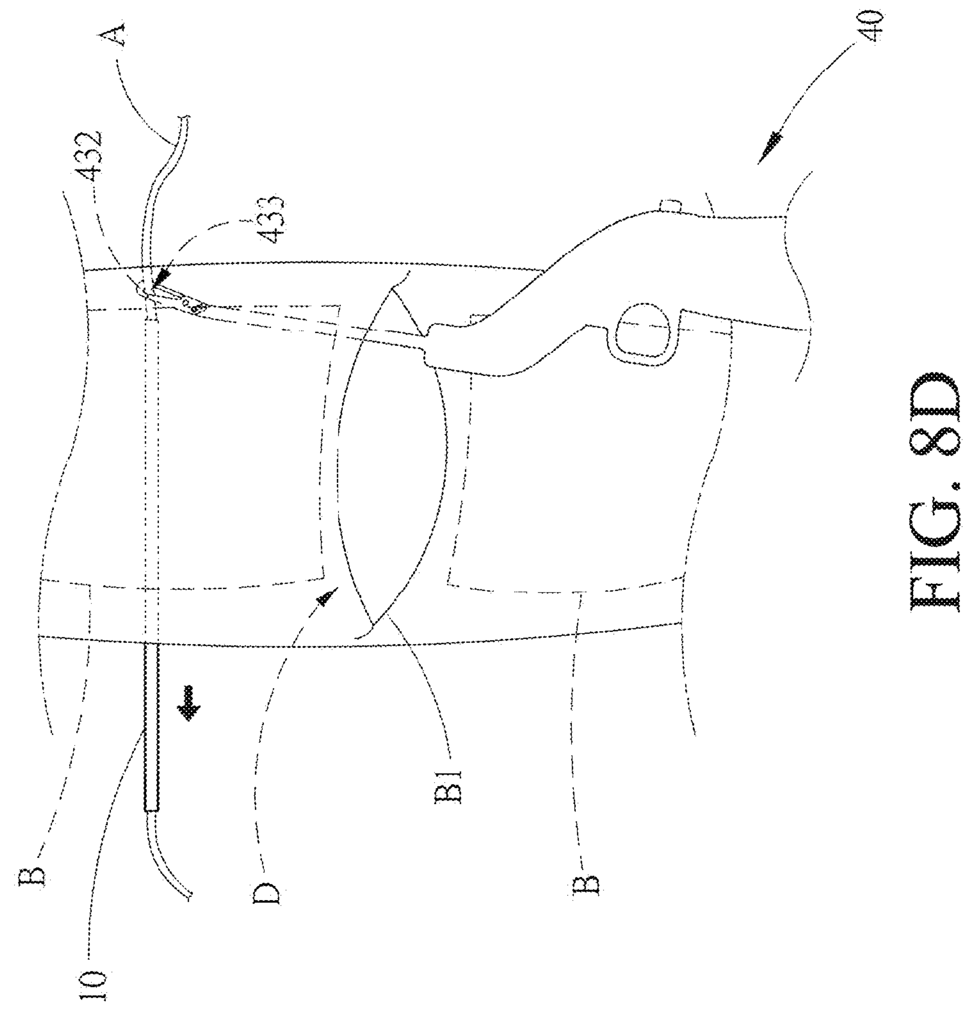
Figure 8E:
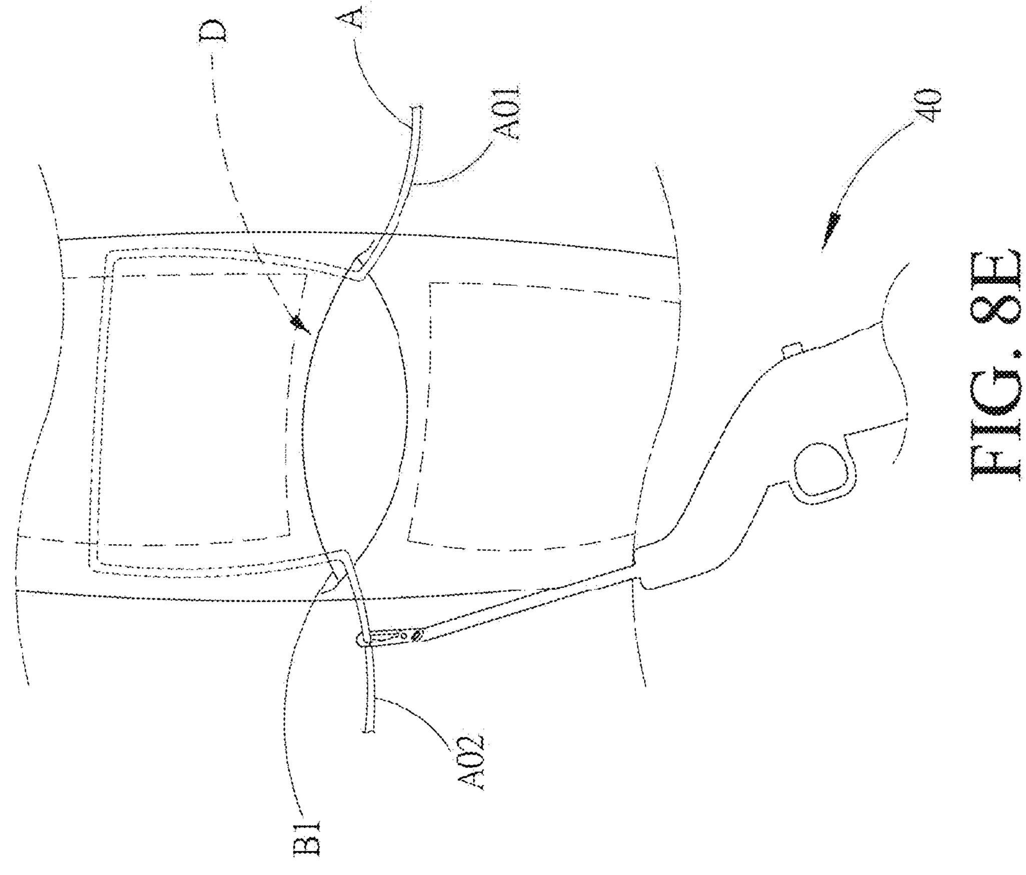

Referring to FIG. 8E, the steps of inserting the holding part 43 through the incision B1, engaging the outer tube 10 with the hook element 432, and moving the outer tube 10 are repeated on the other side of the same wound site B be pierced to pull a second suture end A02 of the suture A to exit through the incision B1 to allow the first suture end A01 and the second suture end A02 to remain outside the incision B1.

Figure 8F:
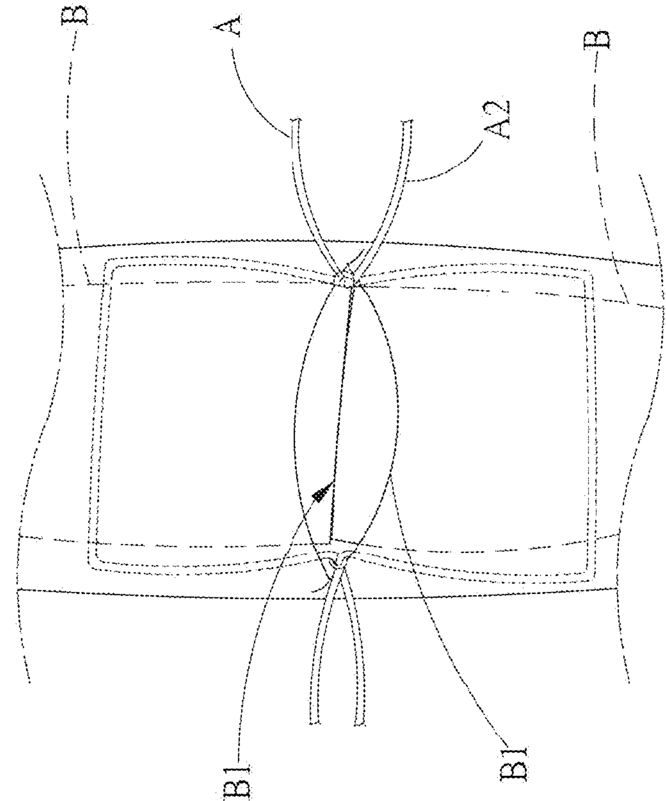
Figure 8G:
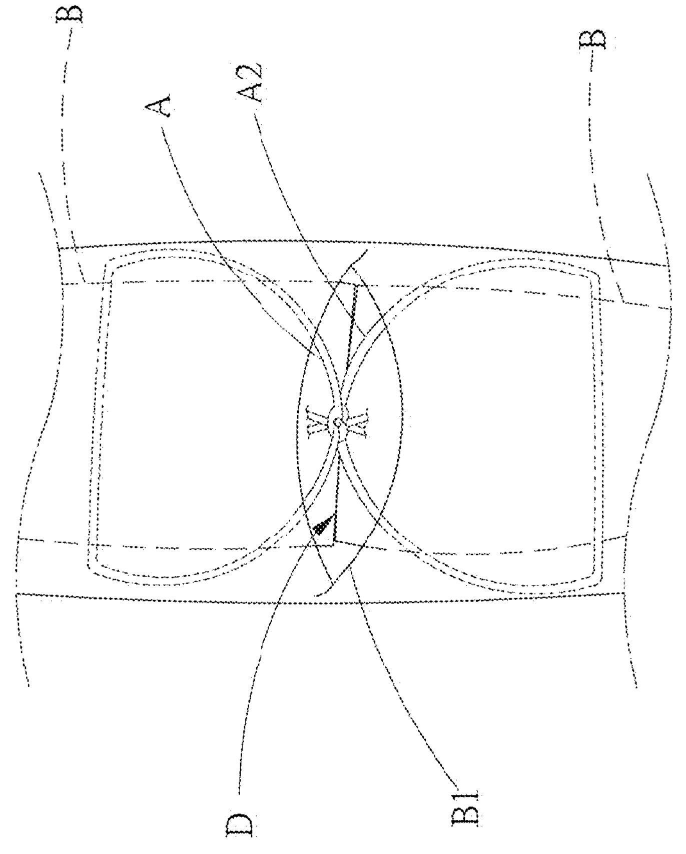

Similarly, referring to FIG. 8F to FIG. 8G, the same steps are repeated to guide another suture A2 to pass through the other wound site B to allow two ends of the another suture A2 to exit through the incision B1. Finally, the two sutures A, A2 which have passed through the two wound sites B respectively, are tightened and tied together at the incision B1, thereby closure of the interspace D is completed.

In the present invention, the method for tying the two sutures A, A2 together is not limited. Two ends of one suture A can be aligned to corresponding ends of another sutures A2 and then tying the two sutures A, A2 together, or the two ends of one of the two sutures A can be tightened with two ends of another suture A2 directly.

Further, as shown in FIGS. 6A to 6D, in the fourth preferred embodiment, the hook element 432 can be fixedly connected to the long tubular part 42, and the closure element 434 is pivotally connected to the hook element 432. A control mechanism 44 is disposed on the handle part 41 and extends through the long tubular part 42 to connect to the closure element 434. The control mechanism 44 allows the closure element 434 to pivot relative to the hook element 432, such that the wire containing space 433 can be opened and closed to loosen or clamp the suture A.

The control mechanism 44 includes an active element 442, a connecting element 444, and a linkage bar 446. The active element 442 is movably disposed within the handle part 41 and is provided with an actuating ring 4422 exposed outside of the handle part 41. The connecting element 444 is movably disposed within the handle part 41 and includes a first elongated slot 4442 formed in the connecting element 444 at one end near the active element 442. The active element 442 has a first shaft 4424 movably held in the first elongated slot 4442. The linkage bar 446 is movably disposed within and extends through the long tubular part 42. One end of the linkage bar 446 is pivotally connected to the end of the connecting element 444 opposite to the active element 442. The closure element 434 includes a second elongated slot 4342 positioned at one end near the linkage bar 446. The linkage bar 446 has a second shaft 4425 movably held in the second elongated slot 4342. By pulling the actuating ring 4422 located outside the handle part 41, the closure element 434 can pivot relative to the hook element 432.

Figure 7A:
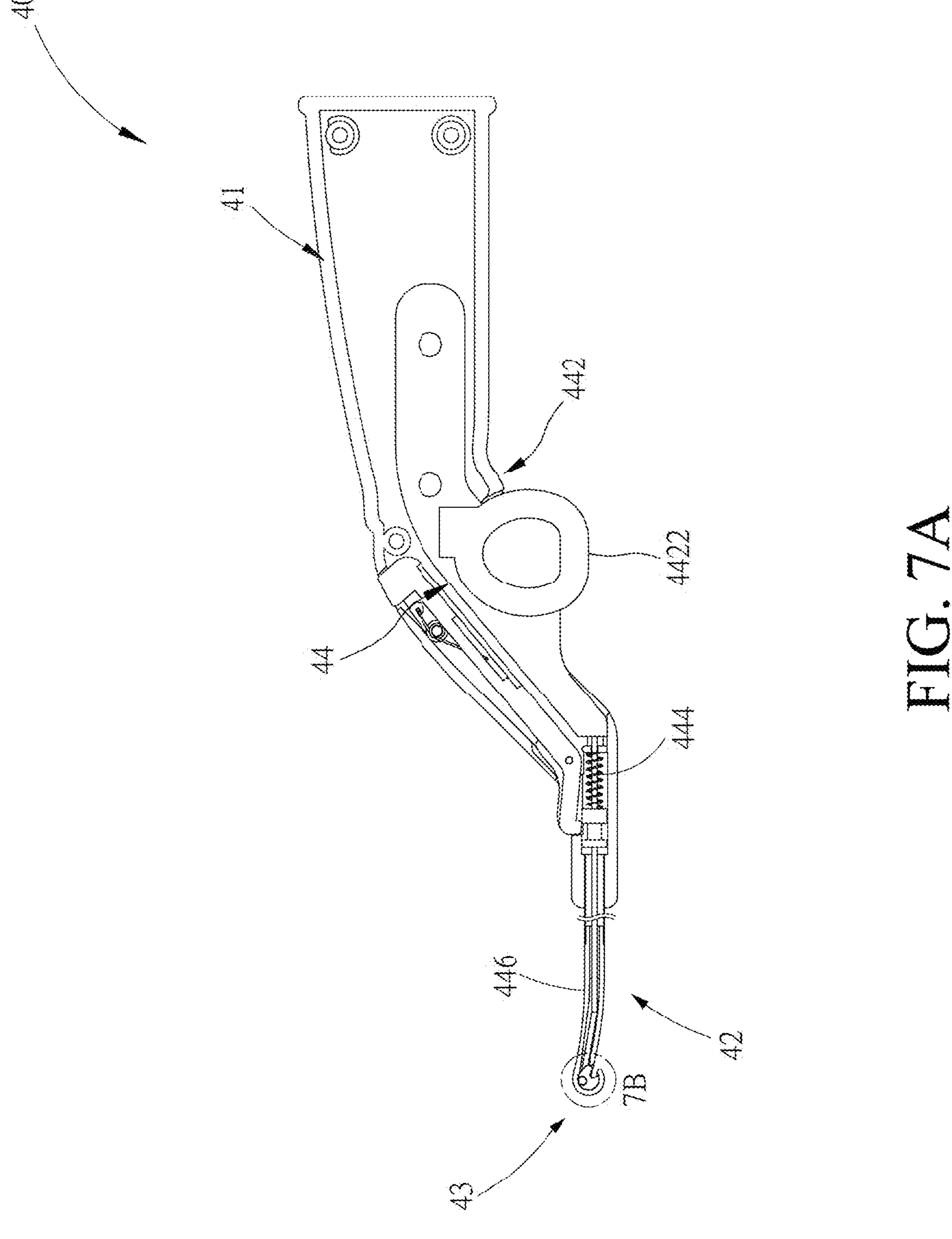
FIG. 7A to FIG. 7D illustrate side views of a fifth preferred embodiment of a thread hooking device of a suture fixation system in accordance with the present invention.
Figure 7B:
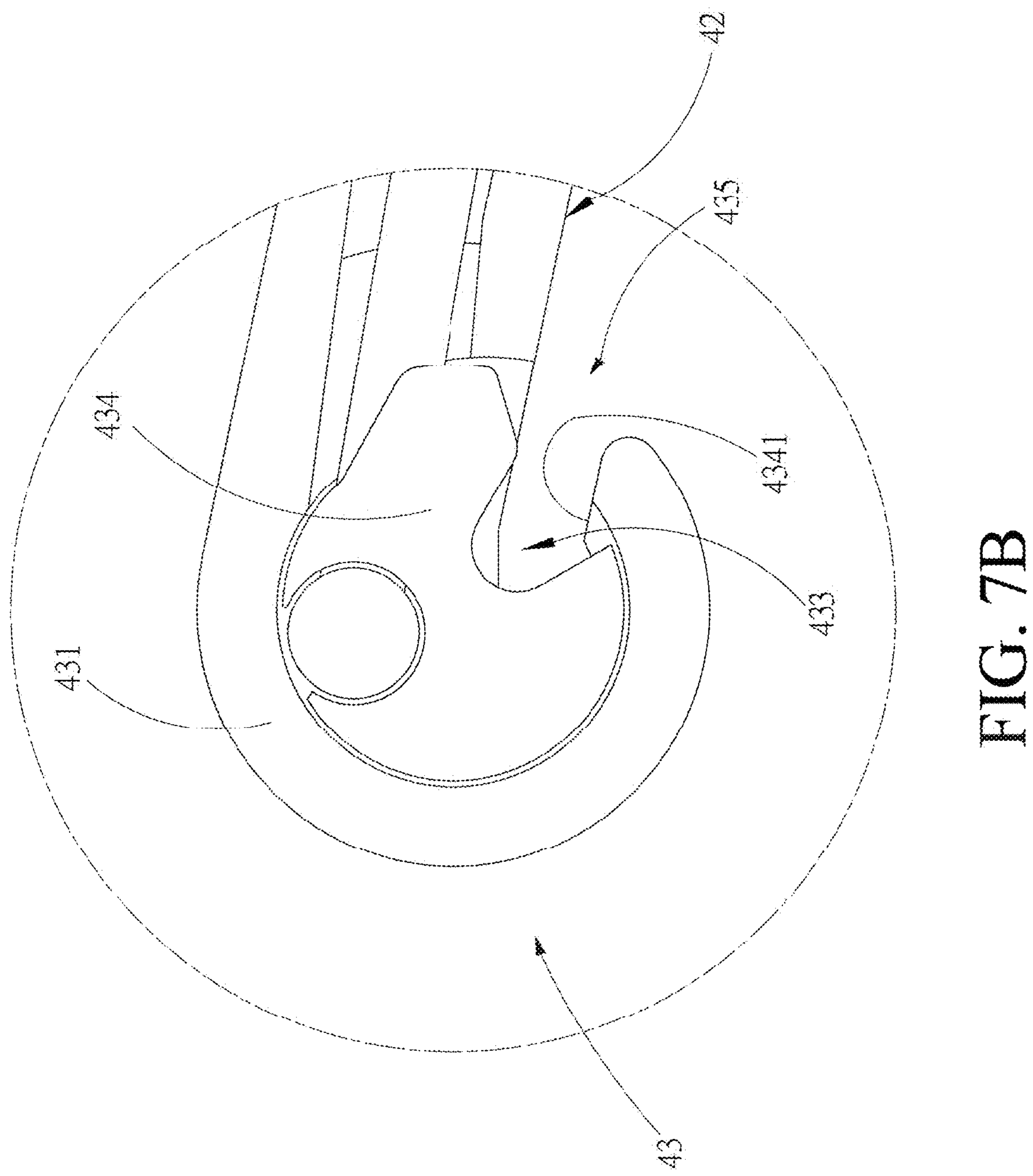
Figure 7C:
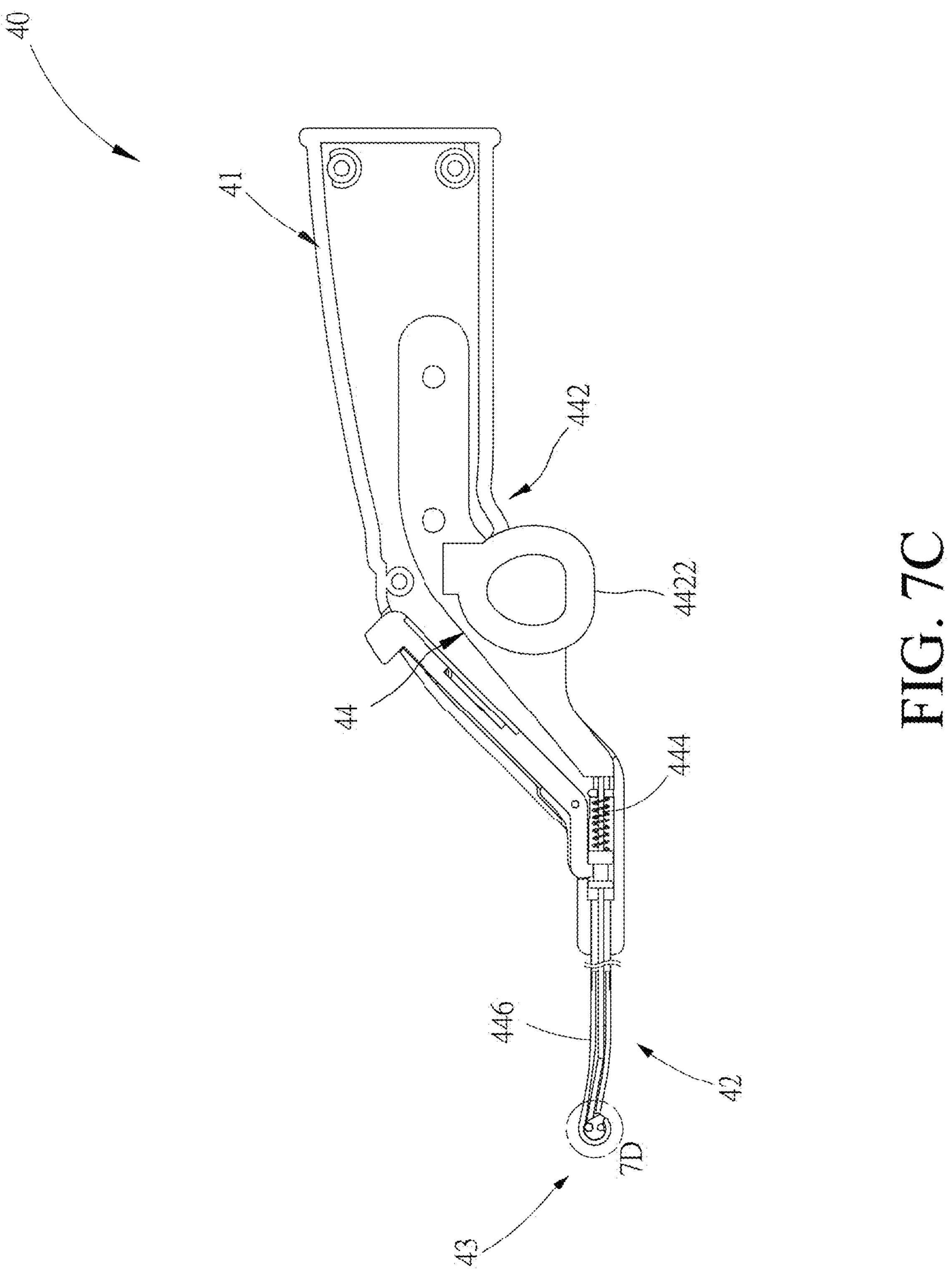
Figure 7D:
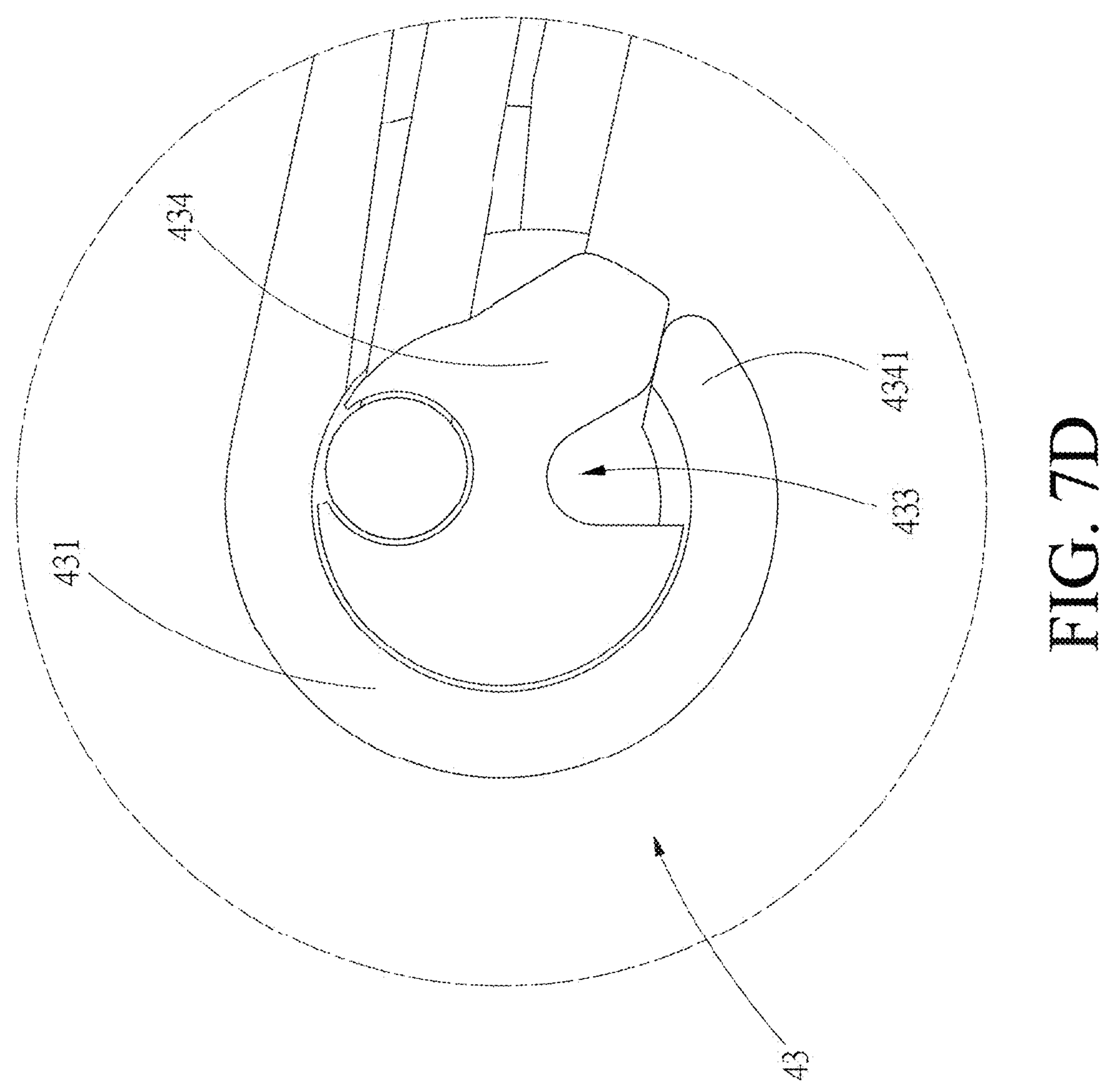

Further, as shown in FIGS. 7A and 7B, a fifth embodiment of a thread hooking device 40 of a suture fixation system is disclosed. In this embodiment, the hook portion 431 is configured as a circular-like hollow shell, with the wire containing space 433 formed inside. An opening port 435 is formed between an end of the hook portion 431 and the long tubular part 42. The closure element 434 is a circular-like block and is rotatably disposed within the hook portion 431. A notch 4341 is radially recessed in a circumferential surface of the closure element 434. When the closure element 434 is rotated within the hook portion 431, at least a portion of the notch 4341 aligns with at least a portion of the opening port 435, thereby the wire containing space 433 is formed.

The control mechanism 44 is disposed on the handle part 41, extends through the long tubular part 42 to be connected to the closure element 434, is configured to control the pivotal movement of the closure element 434 relative to the hook element 432 to allow the closure element 434 to open or close the wire containing space 433. Thus, a suture A can be held or released with the closure or open of the wire containing space 433.

In one embodiment, the connecting element 444 is sleeved with a spring. The spring has two ends respectively abutting against the active element 442 and the linkage bar 446. The linkage bar 446 is movably disposed in and extends through the long tubular part 42, and one end of linkage bar 446 is pivotally connected to the closure element 434.

By pulling the actuating ring 4422 located outside the handle part 41, the closure element 434 is pivoted relative to the hook element 432. The spring is configured to provide an elastic recovery force to allow the closure element 434 to return to the original position.

In another embodiment, additionally, a needle distal end of the guide needle 20 and/or the tube distal end 11 has a bendable structure, which can be manufactured through the design of adjustments, materials, or structural features.

For example, the needle distal end of the guide needle 20 has the bendable structure which is curved, while the tube distal end 11 of the outer tube 10 is a straight rod-like structure. When the needle distal end is positioned in the outer tube 10, the pressure provided by the inner wall of the outer tube 10 makes the guide needle 20 be elastically compressive deformed. Upon protruding from the outer tube 10, the needle distal end of the guide needle 20 reverts to its curved shape of the bendable structure due to elastic recovery, and to form the bendable structure. Thus, the surgical guidewire device can be designed according to the specific needs and shape of the wound site B to show versatile functionality.

What is claimed is:

1. A method for passing a tissue fixation material through a surgical system, the method comprising:

positioning a tissue fixation material in a needle eye structure, the needle eye structure formed at a proximal end of a guide needle;

with the tissue fixation material in the needle eye structure, elastically compressing the needle eye structure and moving the guide needle in a distal direction to pass the tissue fixation material in the distal direction into an outer tube in a first incision in a patient;

moving a hooking device into a second incision in the patient; and positioning the hooking device such that the tissue fixation material and the outer tube are within a hook at a distal end of the hooking device.

2. The method of claim 1, wherein the tissue fixation material is a suture.

3. The method of claim 1, further comprising, with the guide needle, exiting a third incision in the patient.

4. The method of claim 1, further comprising, with a guidewire block, clamping two sides of an outer surface of the outer tubes with a plurality of claws.

5. The method of claim 4, wherein the plurality of claws comprise three claws with an axial staggered and radially spaced arrangement.

6. The method of claim 4, further comprising positioning a slit of the guidewire block radially within the needle eye structure.

7. The method of claim 1, further comprising, with the tissue fixation material in the needle eye structure, positioning a treading structure in the needle eye structure.

8. The method of claim 1, further comprising positioning a second tissue fixation material in an incision in the patient and crossing the second tissue fixation material with the tissue fixation material.

* * * * *